US011718870B2

(12) United States Patent
Astier et al.

(10) Patent No.: US 11,718,870 B2
(45) Date of Patent: Aug. 8, 2023

(54) TUNNELING JUNCTIONS FOR SEQUENCING

(71) Applicant: Roche Sequencing Solutions, Inc., Pleasanton, CA (US)

(72) Inventors: Yann Astier, Livermore, CA (US); Juraj Topolancik, Redwood City, CA (US); Hannes Kuchelmeister, Munich (DE); Frank Bergmann, Iffeldorf (DE); Dieter Heindl, Munich (DE); Nikolaus Klaus-Peter Stengele, Pleiskirchen (DE)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 897 days.

(21) Appl. No.: 16/445,635

(22) Filed: Jun. 19, 2019

(65) Prior Publication Data
US 2019/0390267 A1 Dec. 26, 2019

Related U.S. Application Data

(60) Provisional application No. 62/688,257, filed on Jun. 21, 2018.

(51) Int. Cl.
*C12Q 1/6869* (2018.01)
*C12Q 1/6876* (2018.01)
*G01N 15/10* (2006.01)

(52) U.S. Cl.
CPC ......... *C12Q 1/6869* (2013.01); *C12Q 1/6876* (2013.01); *G01N 15/1031* (2013.01); *G01N 15/1056* (2013.01); *C12Q 2525/117* (2013.01); *C12Q 2535/122* (2013.01); *C12Q 2563/113* (2013.01); *C12Q 2563/116* (2013.01); *C12Q 2563/155* (2013.01); *C12Q 2565/607* (2013.01)

(58) Field of Classification Search
None
See application file for complete search history.

(56) References Cited

U.S. PATENT DOCUMENTS

| | | | |
|---|---|---|---|
| 7,250,115 | B2 | 7/2007 | Barth |
| 8,628,649 | B2 | 1/2014 | Lindsay et al. |
| 8,795,961 | B2 | 8/2014 | Rank et al. |
| 9,395,352 | B2 | 7/2016 | Lindsay et al. |
| 2007/0114180 | A1 | 5/2007 | Ramanathan et al. |
| 2009/0208957 | A1 | 8/2009 | Korlach et al. |
| 2015/0001079 | A1 | 1/2015 | Bai et al. |
| 2015/0142327 | A1 | 5/2015 | Ashcroft et al. |
| 2016/0194698 | A1 | 7/2016 | Lindsay |
| 2018/0031523 | A1 | 2/2018 | Astier et al. |
| 2018/0087102 | A1 | 3/2018 | Nagpal et al. |
| 2018/0180567 | A1 | 6/2018 | Li et al. |

FOREIGN PATENT DOCUMENTS

| | | |
|---|---|---|
| WO | 2017/030999 A1 | 2/2017 |
| WO | 2017/189930 A1 | 11/2017 |

OTHER PUBLICATIONS

Lindsay, Recognition Tunneling, Nanotechnology, 21, 262001, 1-12, 2010. (Year: 2010).*

* cited by examiner

*Primary Examiner* — Angela M. Bertagna
*Assistant Examiner* — Carolyn L Greene
(74) *Attorney, Agent, or Firm* — Kilpatrick Townsend and Stockton LLP

(57) ABSTRACT

Molecules may be analyzed (e.g., sequencing of nucleic acid molecules) by tunneling recognition at a tunneling junction. Embodiments of the present invention may allow detecting individual nucleotides and the sequencing of a nucleic acid molecule using a tunneling junction. By labeling a specific nucleotide with a moiety, tunneling junctions may generate a signal with a suitable signal-to-noise ratio. The tunneling recognition uses a tunneling current that is mostly through the moiety rather than mostly through the nucleotide or a portion of the molecule of interest. Because a single nucleotide can be detected with a signal with a suitable signal-to-noise ratio resulting from the tunneling current passing through the moiety, embodiments of the present invention may allow for fast detection of nucleotides using a tunneling current.

43 Claims, 23 Drawing Sheets

(16 of 23 Drawing Sheet(s) Filed in Color)

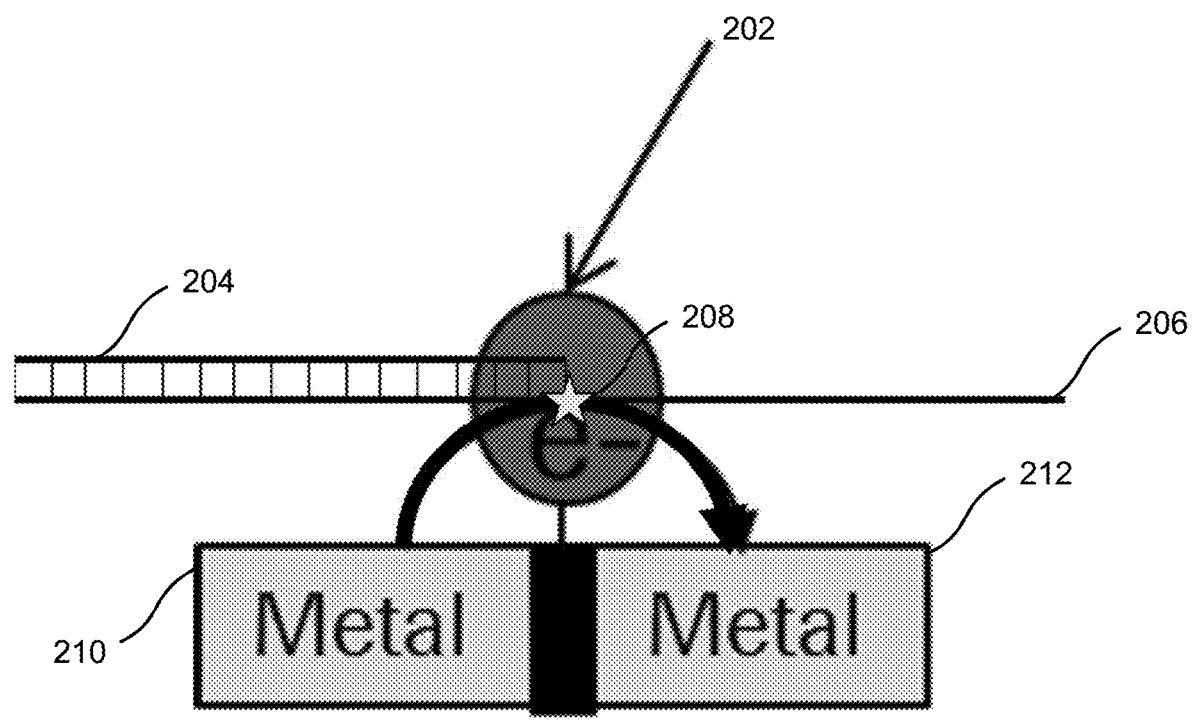
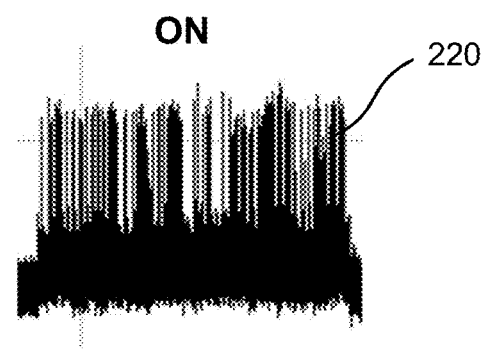
FIG. 2A

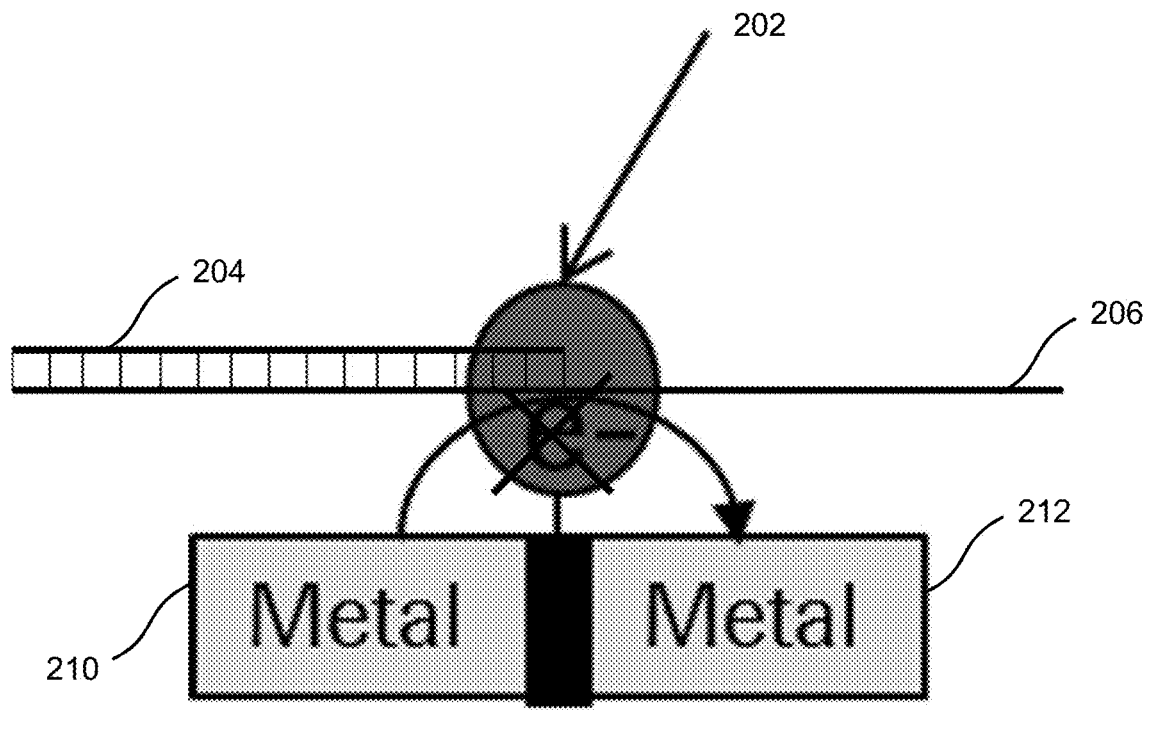
FIG. 2B

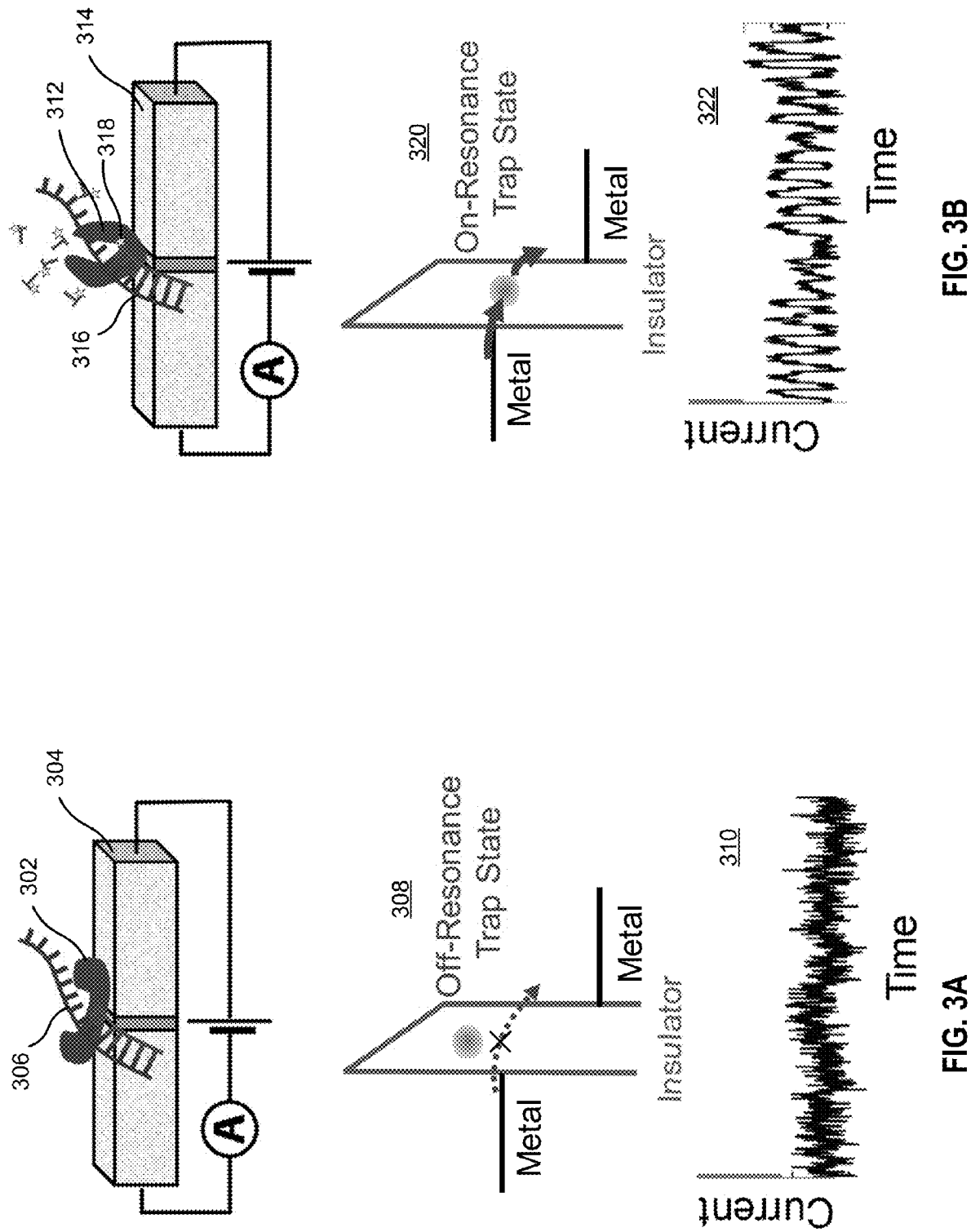

TUNNELING JUNCTIONS FOR SEQUENCING

CROSS-REFERENCES TO RELATED APPLICATIONS

This application claims priority to U.S. Provisional Patent Application 62/688,257 filed Jun. 21, 2018, the disclosure of which is incorporated by reference in its entirety for all purposes.

BACKGROUND

Technologies for analyzing single molecules (e.g. nucleic acids) include tunneling junction devices that have a sub-molecular sized gap between two conducting layers. Tunneling junctions use tunneling recognition. Tunneling recognition is based on placing a molecule or a portion of a molecule (e.g., a nucleotide of a nucleic acid) between conducting layers. When the molecule or the portion of the molecule contacts or is sufficiently close to both layers, the orbitals of the molecule or portion of the molecule will allow electrons to transfer from one layer to the other, creating a tunneling current. The tunneling current can be analyzed to identify the molecule or the portion of the molecule.

To identify portions of the molecule, such as nucleotides, dimensions of the gap would normally have to be on the order of nanometers, including less than 2 nm, or even sub-nanometer. Creating a gap of this small size requires precise and expensive techniques. Reducing dimensions of the tunneling junction may also make contact of the molecule less frequent and for a shorter duration. Additionally, such a small gap size may cause shorts and may lead to a high background tunneling current.

Therefore, improvements in the design and manufacturability of tunnel junctions used in chemical and biological detection and processes involving the devices are still needed. Design and manufacturability improvements should not come at the expense of accurate and precise analysis. These and other issues are addressed by the technology described in this document.

BRIEF SUMMARY

Embodiments of the present invention may allow for the analysis of molecules (e.g., sequencing of nucleic acid molecules) by tunneling recognition at a tunneling junction. The tunneling junction may be an electrical tunneling junction or a magnetic tunneling junction. Embodiments of the present invention may allow detecting individual nucleotides, and thus accurate sequencing of a nucleic acid using a tunneling junction may be achieved. By labeling a specific nucleotide with a moiety, tunneling junctions may generate a binary signal that is clear with a suitable signal-to-noise ratio. The tunneling recognition uses a tunneling current that is mostly through the moiety rather than mostly through the nucleotide or a portion of the molecule of interest.

The tunneling junction devices may focus on reading a single nucleotide at a time. A polymerase attached to a template strand of a DNA molecule may be tethered to a dielectric in a tunneling junction. A double-stranded DNA molecule is synthesized by the polymerase using the template strand. A single type of nucleotide (e.g., A nucleotides) may be labeled with a moiety and introduced to the device. The nucleotide is incorporated into the DNA molecule if it is complementary to the template strand at a current position. The device may include many tunneling junctions, each with a separate polymerase-DNA complex. The device may be washed of excess free nucleotides. If the nucleotide is added to the DNA molecule, then the moiety may cause a current signal in the tunneling junction. If the nucleotide is not added to the DNA molecule, then the current may be near zero. The moiety may then be removed. The next type of labeled nucleotide can be introduced to the device, and the process can be repeated. The current signal generated by the moiety may be higher current than a background current through the nucleotide itself.

Because a single nucleotide can be detected with a signal with a suitable signal-to-noise ratio resulting from the tunneling current passing through the moiety, embodiments of the present invention may allow for fast detection of nucleotides using a tunneling current. By detecting current through the moiety rather than the nucleotide itself, the dielectric in the tunneling junction may be thicker than the size of a single nucleotide. Hence, the tunneling junctions can be manufactured more easily, more cheaply, and more quickly.

The tunneling junction devices may be manufactured with semiconductor processing techniques. The read time for detecting a nucleotide may approach or be equivalent to read times with flash drives. Incorporating a plurality of tunneling junctions into a single sequencing device may allow for multiplexing. Embodiments of the present invention may allow for a number of tunneling junctions similar to the number of tunneling junctions in a flash drive. In other words, billions of tunnel junctions could be incorporated in a device the size of a flash drive (an area on the order of a square centimeter). A highly multiplexed system may enable rapid and accurate sequencing.

A better understanding of the nature and advantages of embodiments of the present invention may be gained with reference to the following detailed description and the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 2A and 2B show diagrams of the tunneling current through a nucleotide with and without a moiety according to embodiments of the present invention.

FIGS. 3A and 3B show the tunneling current response to a nucleotide with and without a moiety according to embodiments of the present invention.

TERMS

Figure 1:
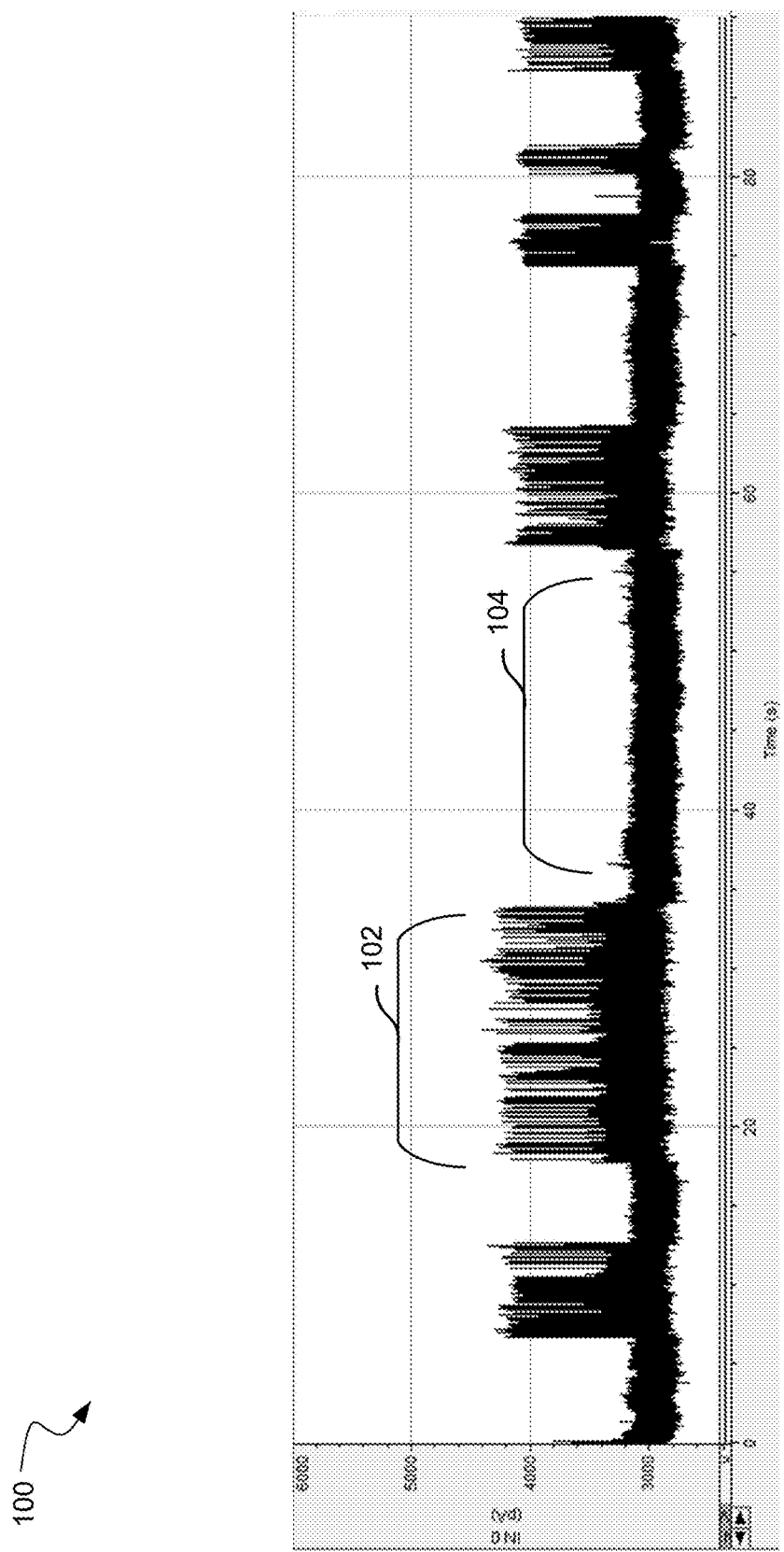
FIG. 1 shows a graph of Random Telegraphic Noise (RTN) according to embodiments of the present invention.

The term "contacting" may refer to bringing one object in proximity to another object such that electrons may tunnel from one object through the other object. At a subatomic level, two objects may never physically touch each other as repulsive forces from electron clouds in the objects may prevent the objects from coming into closer proximity.

"Nucleic acid" may refer to deoxyribonucleotides or ribonucleotides and polymers thereof in either single- or double-stranded form. The term may encompass nucleic acids containing known nucleotide analogs or modified backbone residues or linkages, which are synthetic, naturally occurring, and non-naturally occurring, which have similar binding properties as the reference nucleic acid. Examples of such analogs may include, without limitation, phosphorothioates, phosphoramidates, methyl phosphonates, 2-O-methyl ribonucleotides, locked nucleic acids (LNAs), peptide nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

The term "nucleotide," in addition to referring to the naturally occurring ribonucleotide or deoxyribonucleotide monomers, may be understood to refer to related structural variants thereof, including derivatives and analogs, that are functionally equivalent with respect to the particular context in which the nucleotide is being used (e.g., hybridization to a complementary base), unless the context clearly indicates otherwise.

The term "oscillate" may refer to the motion of an object in a fluid as a result of Brownian motion or other forces. An object may oscillate without active intervention by a person or a machine. In some cases, an object may oscillate as a result of an applied electric field or a pressure-driven flow.

The term "moiety" may include a functional group, as the technical term is used in chemistry. In addition, moiety may also refer to an atom or group of atoms bonded together that may form part of a larger compound. Moieties may include magnetic nanoparticles.

Directional terms such as "above" or "on top of" for semiconductor processing layers and steps may use a reference frame where these terms designate a position farther away from a plane defined by a surface of the substrate. The "bottom" may be the underside of a substrate or toward the underside of the substrate. One of skill would understand that even if a substrate is processed upside-down, the "bottom" of a layer may still refer to a side of the layer closest to the underside or non-processed side of a substrate.

The term "electrical characteristic" may be understood to refer to any property related to an electrical circuit. Electrical characteristic may refer to voltage, current, resistance, impedance, inductance, or capacitance, and time variations thereof (e.g., current frequency).

DETAILED DESCRIPTION

Tunneling recognition is a technique used to identify molecules or portions of molecules (e.g., a nucleic acid). A tunneling junction may include an electrical tunneling junction or a magnetic tunneling junction. An electrical tunneling junction may include two conductors sandwiching an insulating layer. When a molecule or a portion of the molecule contacts both conductors or is sufficiently close to both conductors, the current tunneling from one conductor to the other changes. The molecule or portion of the molecule may change the amplitude of the current by inducing direct conduction or trap-assisted tunneling.

A magnetic tunneling junction may include two ferromagnetic materials sandwiching an insulating layer. When a magnetic nanoparticle is close to the ferromagnetic materials, the relative orientation of the magnetic domains changes and the current tunneling from one conductor to the other changes. The amount of tunneling current depends on the orientation of the magnetization (i.e., the spin) of the ferromagnetic materials. The current for ferromagnetic materials having the same spin (i.e., being parallel) is higher than two ferromagnetic materials having opposite spin (i.e., being antiparallel).

With either junction, the tunneling current may vary depending on the identity of the molecule or portion of the molecule that contacts both conductors and how much the molecule oscillates between contacting and not contacting the conductors. If the current through only a single nucleotide of a nucleic acid is to be measured, the insulating layer would typically have to be less than the size of a nucleotide so that the nucleotide can contact both conductors across the insulating layer.

However, even a thickness of 1 nm is about the size of three nucleotides, which can cause problems for detection of a single nucleotide. Even when the thickness of the insulating layer is on the order of 1 to 2 nm, manufacturing may still be difficult, and the background tunneling current through the thin insulating layer may be too large to detect a signal from the nucleotide or such a thin insulating layer may not prevent shorting. Increasing the thickness of the insulating layer may allow for easier manufacturing, but then a measurable tunneling current would need to pass through even more nucleotides. A signal passing through multiple nucleotides would involve more complicated signal analysis to identify the individual nucleotides.

Embodiments of the present technology can reduce the noise in a current signal and do not require a thin insulating layer on the order of 1 to 2 nm. The tunneling junction devices may focus on reading a single nucleotide at a time. A polymerase may be tethered to a tunneling junction (e.g., to the insulating layer). A double-stranded DNA molecule may be synthesized by the polymerase from a template parent strand. Embodiments may include many tunneling junctions on the same device, allowing high multiplexing.

In some embodiments, a set of nucleotides of a single type (e.g., A nucleotides) are labeled with a moiety and introduced to the device. These nucleotides may be added to a nascent strand when the nucleotides are of a type complementary to the template parent strand. The device may be washed of excess free nucleotides at this time or later in a cycle after introducing additional labeled nucleotides. If the nucleotide is added to the DNA molecule, then the moiety causes a current signal in the tunneling junction. If the nucleotide is not added to the DNA molecule, then the current may be near zero. The moiety may then be removed. A next type of labeled nucleotide can be introduced to the device, and the process may be repeated, thereby allowing a detection of whether a particular nucleotide is incorporated at each position. The current signal generated through the moiety may be higher than a background current through the nucleotide itself, thereby providing a signal with less noise.

I. USING RANDOEM TELEGRAPHIC NOISE (RTN)

A tunneling current through the nucleotide or nucleotides themselves may not generate a high enough current signal with a suitable signal-to-noise ratio. The nucleotide may be in contact with the conductors for a short duration and the differences in tunneling currents between different nucleotides or sequences of nucleotides may be small. Accordingly, stronger and more easily detectable signals are desired.

A. RTN

To generate a current signal with a suitable signal-to-noise ratio, the current signal of embodiments of the present invention may mimic Random Telegraphic Noise (RTN), which previously referred to a problem with unwanted current signals in tunneling junctions. Without intending to be bound by a particular theory, one explanation for RTN is that impurities cause the unwanted current signals. The impurities may have trapped a charge and may sustain a higher current for a significant duration. The impurities may be imperfections in the oxide of the tunneling junction that act like charge traps. These impurities may include oxygen vacancies in the oxide, ions trapped in the metal oxide matrix, and substitute ions (e.g., dopants). After the impurity is no longer trapped the charge or the impurity left, the current drops. The devices in embodiments of the present invention intentionally recreate this RTN phenomenon with the tag of the labeled nucleotide.

FIG. 1 shows a graph 100 of RTN in a plot of current versus time. The graph shows areas of higher current (e.g., area 102) and areas of lower, near-zero current (e.g., area 104). The areas of higher current may have a trapped charge, while the areas of lower current may not have a trapped charge. The analysis of whether a charge may be trapped may then depend on identifying where a higher current than the background current is present.

B. Usage of Moiety

To intentionally mimic RTN, a moiety that generates RTN can be attached to the molecule of interest. For example, if the molecule to be analyzed is a nucleic acid, a moiety can be attached to a nucleotide to be incorporated into a growing nucleic acid strand.

FIGS. 2A and 2B show how a moiety may be used to generate a current signal. A DNA polymerase 202 is elongating a nascent strand 204, which is being hybridized to a template parent strand 206. In FIG. 2A, the last nucleotide added to nascent strand 204 includes moiety 208. Moiety 208 allows for an electron to tunnel from a first conductor 210 to a second conductor 212. Tunneling electrons may generate a current signal versus time similar to graph 220. The random nature of the current signal may be a result of capture and release of the trapped charge state and/or capacitive effects (i.e., charge and discharge). The capacitive effects may result from a trapped electron changing the charge distribution around the tunneling junction, which may change the height of the tunneling barrier. The amplitude of the current flowing through the junction may depend exponentially on the barrier height. Small changes in the barrier height caused by random charging and discharging of the trap state may result in large changes in the tunneling current, which are evident in FIG. 2A.

In FIG. 2B, when no moiety is present, an electron cannot tunnel from first conductor 210 to second conductor 212. In FIG. 2B, the tunneling current should be near zero or near the background tunneling current, similar to graph 222. Hence, moiety 208 and therefore a nucleotide may be detected by measuring a tunneling current greater than zero or the background tunneling current.

The moiety should be an entity that allows the tunneling current to pass through based on a certain potential applied. FIG. 3A shows the tunneling current response when no moiety is attached to a nucleotide. A polymerase 302 is attached to a tunneling junction 304. Polymerase 302 is hybridizing template parent strand 306. No moiety is present, and no charge is trapped. The tunneling junction is in an off-resonance trap state 308, which does not allow current to tunnel from one conductor to the other conductor. The result is a graph 310 of current versus time where the current is near zero and at a background level.

FIG. 3B shows the tunneling current response when a moiety is attached to a nucleotide. A polymerase 312 is attached to a tunneling junction 314. Polymerase 312 is hybridizing template parent strand 316. The nucleotide added has a moiety 318. Moiety 318 traps a charge at the electron transfer frequency. The tunneling junction is in an on-resonance trap state 320. A current can tunnel from one conductor through the moiety to the other conductor. The result is a graph 322 of current versus time where the current reaches a non-zero current and a current above a background level.

II. LABEL COMPOUND WITH MOIETY

The moiety used may be part of a label compound including more components than solely the moiety. The chemical compound used in methods and systems described herein may include a nucleotide, a cleavable linker, and a moiety. The nucleotide may include any of the four DNA nucleotides including adenine (A), thymine (T), guanine (G), and cytosine (C). The nucleotide may also include the four RNA nucleotides, including adenine, uracil (U), guanine, and cytosine. The label compound may be sufficiently long to allow contact of the moiety with the tunneling junction as the nucleotide is being hybridized to the template parent strand.

A. Composition

For electrical tunneling junctions, the moiety may be selected from the group consisting of an organometallic group, a nanoparticle, a conjugated aromatic group, and a conductive organic molecule. Conductive organic molecules may have no bandgaps and may not be insulators or semiconductors. As examples, organometallic groups may include ferrocene, metal phthalocyanines, ruthenium, osmium, and transition metal organometallic compounds. As examples, nanoparticles may include gold, silver, platinum, magnesium, or titanium nitride nanoparticles. Nanoparticles may include any particles having a characteristic size from 1 to 10 nm, including from 1 to 5 nm and from 5 to 10 nm. The characteristic size may be the diameter of the nanoparticle if the nanoparticle is a sphere. However, if the nanoparticle is not a sphere, the characteristic size may be the diameter of a sphere having the same volume as the non-spherical nanoparticle. In some instances, the characteristic size may be the minimum of the width, length, or height of a nanoparticle. Conjugated aromatic groups may include a compound with several benzene rings, including a compound with two to nine benzene rings, anthracene, phenanthrene, tetracene, chrysene, triphenylene, pyrene, pentacene, benzopyrene, corannulene, benzoperylene, coronene, ovalene, and benzofluorene. The conjugated aromatic group may include a compound with benzene rings arranged in linear structure. As examples, conductive organic molecules may include short polymers including poly-pyrrole and poly-aniline.

The moiety, as mentioned above, may allow for a tunneling current by holding a charge in an on-resonance trap state. In some embodiments, the same moiety may be attached to the four nucleotides. In other embodiments, different moieties may be used for different nucleotides, with each moiety generating a different tunneling current for an applied voltage. The moiety may comprise multiple groups, such as multiple organometallic groups.

For magnetic tunneling junctions, the moiety may be selected from the group consisting of a ferromagnetic or superparamagnetic material. Materials may include a magnetic nanoparticle (e.g., FePt, FeCuPt, $Fe_2O_3$). A nanoparticle may have a diameter or characteristic size less than 1 μm, 500 nm, 100 nm, or 10 nm.

The chemical compound may have a structure represented by N—X—S-M, where N is the nucleotide, X is the cleavable linker, S is a spacer, and M is the moiety. The nucleotide may be bonded directed to the cleavable linker.

The cleavable linker may allow the label compound to be cleaved from the incorporated nucleotide after detection. Cleavable linkers are known in the art and have been described e.g., in U.S. Pat. Nos. 7,057,026, 7,414,116 and continuations and improvements thereof. In some embodiments, the label is attached to the 5-position in pyrimidines or the 7-position in purines via a linker comprising an allyl or azido group. In other embodiments, the linker comprises a disulfide, indole or a Sieber group. The linker may further contain one or more substituents selected from alkyl ($C_{1-6}$) or alkoxy ($C_{1-6}$), nitro, cyano, fluoro groups or groups with similar properties. Briefly, the linker can be cleaved by water-soluble phosphines or phosphine-based transition metal-containing catalysts. Other linkers and linker cleavage mechanisms are known in the art. For example, linkers comprising trityl, p-alkoxybenzyl esters and p-alkoxybenzyl amides and tert-butyloxycarbonyl (Boc) groups and the acetal system can be cleaved under acidic conditions by a proton-releasing cleavage agent. A thioacetal or other sulfur-containing linker can be cleaved using a thiophilic metals, such as nickel, silver or mercury. Cleavage protecting groups can also be considered for the preparation of suitable linker molecules. Ester- and disulfide containing linkers can be cleaved under reductive conditions. Linkers containing triisopropyl silane (TIPS) or t-butyldimethyl silane (TBDMS) can be cleaved in the presence of F ions. Photocleavable linkers cleaved by a wavelength that does not affect other components of the reaction mixture include linkers comprising O-nitrobenzyl groups. Linkers comprising benzyloxycarbonyl groups can be cleaved by Pd-based catalysts.

As examples, the cleavable linker X may be cleavable by a metal catalyst (e.g., an allyl group), an enzyme (e.g., protease cleavage site, Tobacco Etch Virus [TEV] cleavage site), light (e.g., nitrobenzene), reduction (e.g., disulfide), an acid (e.g., acetals, methoxymethyl, or protected acetals [e.g., O—$CH_2$—$N_3$ or —O—$CH(N_3)$—]), a base (e.g., succinate, acetyl), oxidation (e.g., vicinal diols), or a phosphatase (e.g., phosphate). The cleavable linker may include —O—$NH_2$, which may be cleaved with nitrite.

As examples, the spacer may be a polyethylene glycol (PEG), alkyl or aryl spacer, peptide, cationic spacer (e.g., spermine), nucleic acid, carbohydrate, or combinations thereof.

Figure 4A:
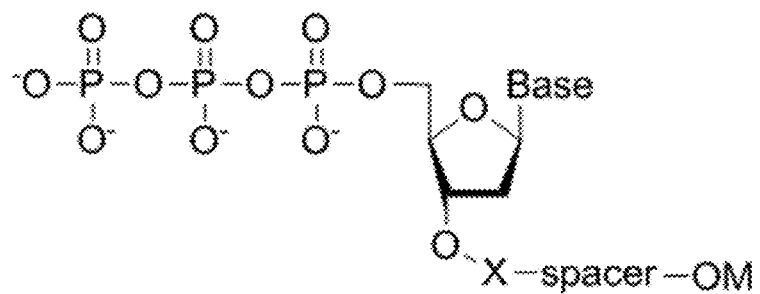
FIGS. 4A, 4B, and 4C show examples of a chemical compound that are modified nucleotides labeled with an organometallic moiety (OM) according to embodiments of the present invention.

FIG. 4A shows an example of a chemical compound. In FIG. 4A, the linker-spacer-moiety is attached to the 3' OH group of the deoxyribose sugar. The nucleotide is linked to X, the cleavable linker, a spacer, and then a organometallic (OM) moiety. Blocking the 3'-OH group may automatically terminate the polymerase reaction. However, a 3'-OH with a bulky compound may not be readily accepted by polymerases.

Figure 4B:
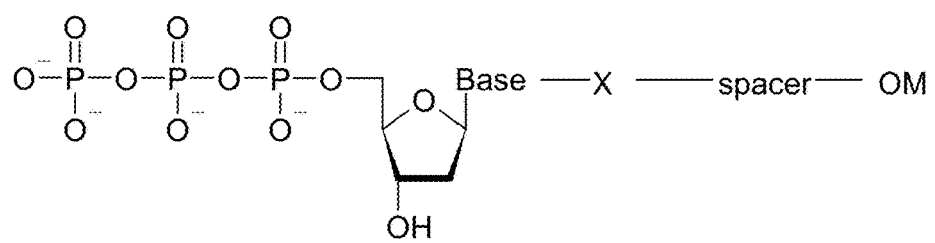

FIG. 4B shows an example of another chemical compound. The linker-spacer-moiety is attached to the base of the nucleotide. Modifying the base is usually well accepted by polymerases. However, because the 3'-OH group is not blocked, the compound in FIG. 4B may lead to less than 100% termination.

Figure 4C:
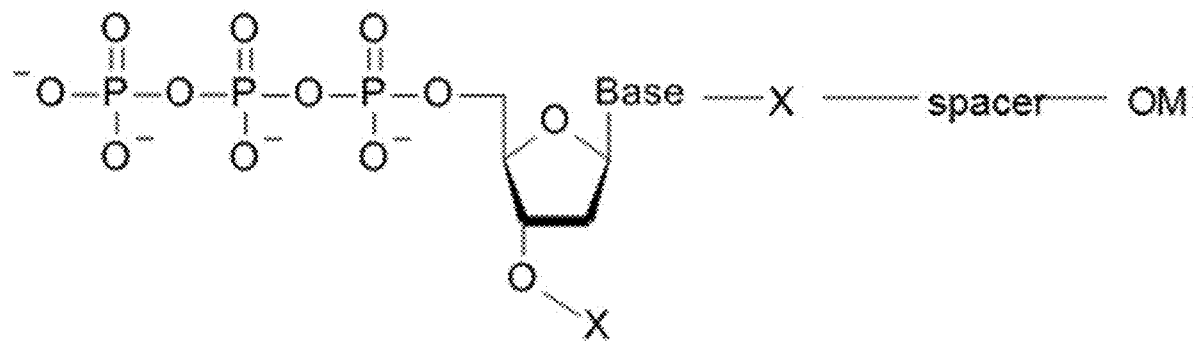

FIG. 4C shows yet another example of a chemical compound. Both the base and the 3' OH group can be bonded to a cleavable linker X. The linker X bonded to the base may be the same linker as X bonded to the 3' OH group. However, in some embodiments, the two linkers may be different compounds. The compound in FIG. 4C may incorporate the advantages of both the compound in FIG. 4A and the compound in FIG. 4B. Adding a small cleavable terminator group at the 3'-OH group may ensure a stop after incorporation. Attaching a large X—S-M compound onto the base may not disturb the polymerase too much. However, FIG. 4C may need to be cleaved at two sites instead of just one site.

The linker-spacer-moiety may act as a lightning terminator (Stupi, B. P. et al., "Stereochemistry of benzylic carbon substitution coupled with ring modification of 2-nitrobenzyl groups as key determinants for fast-cleaving reversible terminators," *Angew. Chem. Int. Ed.*, 51, 1724-1727 (2012) or as a virtual terminator (Bowers, J. et al., "Virtual terminator nucleotides for next-generation DNA sequencing," *Nature Methods*, 6, 593-595 (2009).

The chemical compound may also include a terminator. The terminator may stop a polymerization process. For example, with a polymerase, the terminator may stop the polymerase from adding nucleotides until the terminator is removed. The linker, spacer, moiety, or the combination thereof may act as a terminator. The label compounds in FIGS. 4A, 4B, and 4C may each include a terminator.

If the molecule to be analyzed is not a nucleic acid, the chemical compound may be adapted accordingly. The label compound may be attached to a single unit of a biological polymer. For example, if the chemical compound to be analyzed is a protein, the label compound may be attached to an amino acid instead of a nucleotide.

B. Characterizing Moieties

Figure 5A:
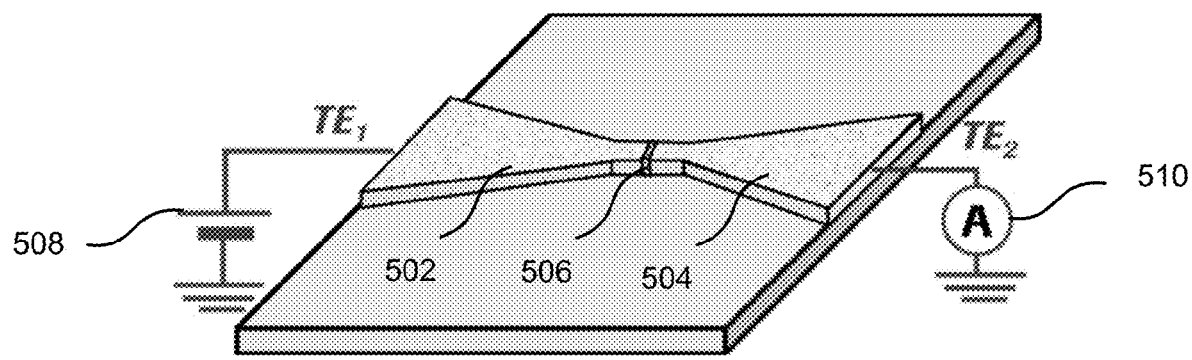
FIGS. 5A, 5B, and 5C show configurations that can be sued to identify suitable moieties according to embodiments of the present invention.
Figure 5B:
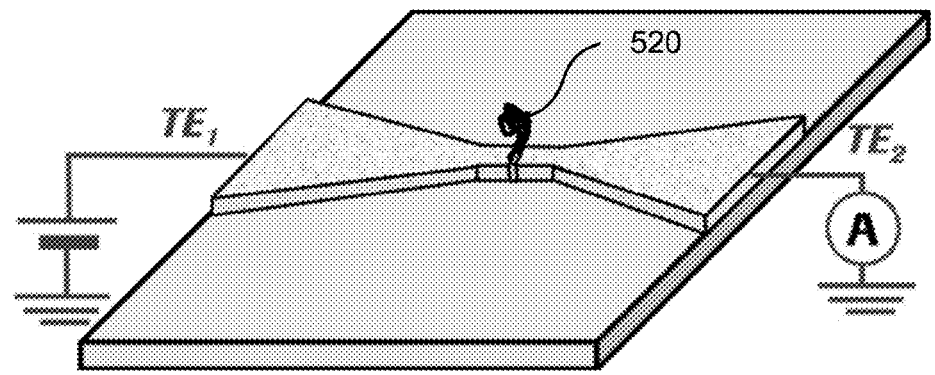
Figure 5C:
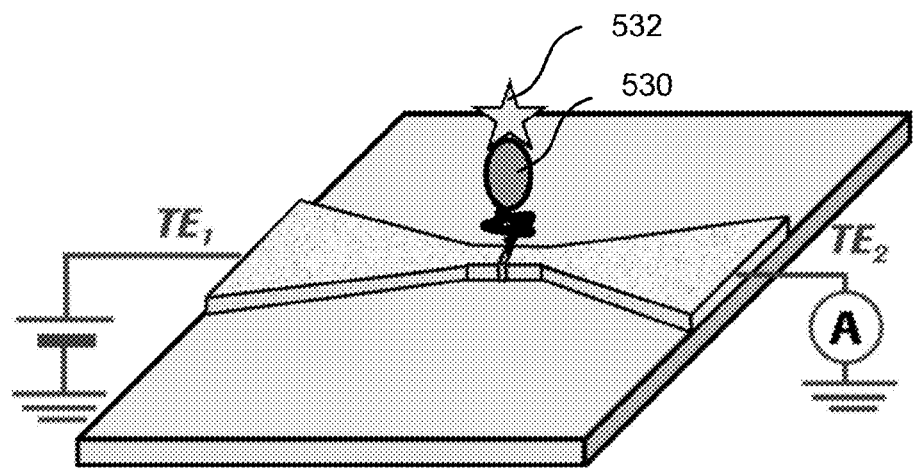

FIGS. 5A, 5B, and 5C show configurations that can be used to identify suitable moieties. FIG. 5A shows an electrical tunneling junction with a first electrode 502, a second electrode 504, and an insulating layer 506. First electrode 502 is connected to power source 508, and second electrode 504 is connected to current meter 510. The electrodes are conductors. The width of either electrode adjacent to insulating layer 506 may be about 50 nm, from 45 nm to 55 nm, from 40 nm to 60 nm, or from 35 nm to 65 nm. The height of either electrode may be 20 nm, from 15 nm to 25 nm, or from 10 nm to 30 nm. The junction area (i.e., the area of the interface between insulating layer 506 and either electrode) may be on the order of $10^3$ nm$^2$ or $10^2$ nm$^2$. The sensing area (i.e., the area of insulating layer exposed for contact with a moiety or other compound to be sensed) is about 20 nm$^2$.

FIG. 5B shows a tether compound 520 attached to insulating layer 506. Tether compound 520 may be hydroquinone SpyTag. SpyTag is a short peptide that forms an isopeptide bond upon encountering its protein partner, SpyCatcher (Reddington, S. C. et al., "Secrets of a covalent interaction for biomaterials and biotechnology: SpyTag and SpyCatcher," *Current Opinion in Chemical Biology*, 2015, 29:94-99, available at dx.doi.org/10.1016/j.cbpa.2015.10.002).

FIG. 5C shows a compound 530 with a moiety 532. Compound 530 is attached to tether compound 520. Compound 530 may include SpyCatcher. Moiety 532 may be any of the possible types of moieties described herein. The tunneling current through moiety 532 can be characterized for the magnitude and other characteristics of the current. Additional types of moieties can be tested. The best performing moieties would be selected based on those that generate the best signal intensity, including amplitude and duration. From the data for different moieties, suitable types of moieties can be selected. Moieties may be selected for a strong, stable current signal. In some embodiments, a plurality of types of moieties, each having a current signal distinguishable from the others, may be identified. The plurality of types of moieties may be used to label different types of nucleotides.

III. METHODS OF ANALYZING MOLECULE

A tunneling junction may be an electrical tunneling junction or a magnetic tunneling junction. Both types of tunneling junctions have commonalities in methods and in the system. Either tunneling junction may be used to determine a sequence of a nucleic acid using a sequencing device. The method may include adding a set of nucleotides to the sequencing device. Each nucleotide of the set of nucleotides may be attached to a label compound. The label compound may include a moiety. The sequencing device may include a junction. The junction may include a first conductor and a second conductor separated by an insulating layer.

Methods may further include elongating a nascent strand using a polymerase attached to the tunneling junction and connected to a template parent strand to be sequenced. Elongating may include the polymerase incorporating a first nucleotide of the set of nucleotides into the nascent strand via hybridization to the template parent strand.

Methods may include measuring a value of an electrical or magnetic characteristic through the first conductor, a first moiety of a first label compound attached to the first nucleotide, and the second conductor. Methods may include detecting the first nucleotide as being hybridized to the template parent strand using the value of the electrical or magnetic characteristic.

Methods specific for electrical tunneling junctions and magnetic tunneling junctions are described below.

A. Electrical Tunneling Junction Configurations

Figure 6:
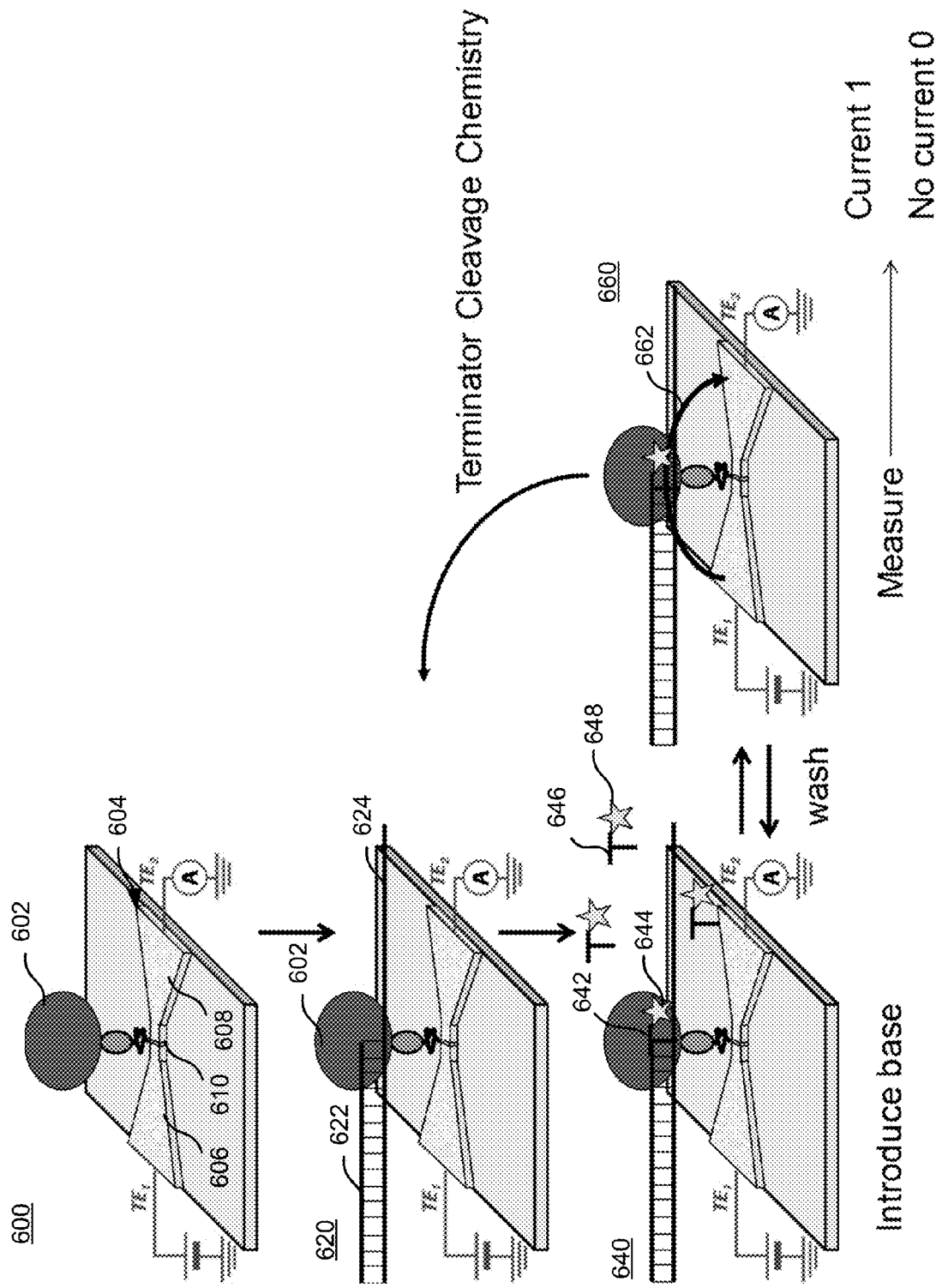
FIG. 6 shows a method of determining a nucleic acid sequence according to embodiments of the present invention.

FIG. 6 illustrates configurations used in determining a nucleic acid sequence. In configuration 600, a polymerase 602 is attached to a tunneling junction 604. Tunneling junction 604 is an electrical tunneling junction. Tunneling junction 604 may include a first electrode 606, a second electrode 608, and an insulating layer 610. First electrode 606 and second electrode 608 are examples of conductors described for tunneling junctions. Insulating layer 610 may separate first electrode 606 and second electrode 608. Tunneling junction 604 may be any tunneling junction described herein and is discussed in greater detail below.

In configuration 620, polymerase 602 is elongating nascent strand 622, which is being hybridized to template parent strand 624 to form a double-stranded nucleic acid molecule.

Configuration 640 illustrates the system after a first liquid with a first nucleotide 642 and a plurality of second nucleotides are contacted with tunneling junction 604. First nucleotide 642 with a first moiety 644 is added to nascent strand 622. First nucleotide 642 may be near polymerase 602. First moiety 644 may contact tunneling junction 604 or be sufficiently close to first electrode 606 and second electrode 608 such that electrons can tunnel through first moiety 644 and the electrodes. A plurality of second nucleotides with second moieties, such as second nucleotide 646 with second moiety 648, may remain in the liquid near tunneling junction 604.

Configuration 660 shows tunneling junction 604 after the plurality of second nucleotides have been removed and a tunneling current 662 through first moiety 644 is being measured. When the current is greater than the background tunneling current, a binary signal of 1 may be generated to show the presence of the first nucleotide, as shown in configuration 660. If the current does not exceed the background tunneling current, a signal of 0 may be generated to show the absence of the first nucleotide. In some embodiments, the current signal may not be binary but instead depend on a magnitude of the current generated by a specific type of first moiety 644.

Because the first nucleotide incorporated by the polymerase into the nascent strand is complementary to the nucleotide on the template parent strand, the complementary nucleotide on the template parent strand may also be identified. For example, in FIG. 6, first nucleotide 642 may be identified, which would also lead to the identification of the complementary nucleotide on template parent strand 624. Either nucleotide may be part of the nucleic acid sequence that is determined by methods described herein.

First nucleotide 642 may be attached to a terminator, which prevents further elongation of nascent strand 622. Removing the terminator attached first nucleotide 642 and first moiety 644 returns the system to a configuration similar to configuration 620, with the exception being that nascent strand 622 includes first nucleotide 642.

B. Example Method With Electrical Tunneling Junction

Figure 7:
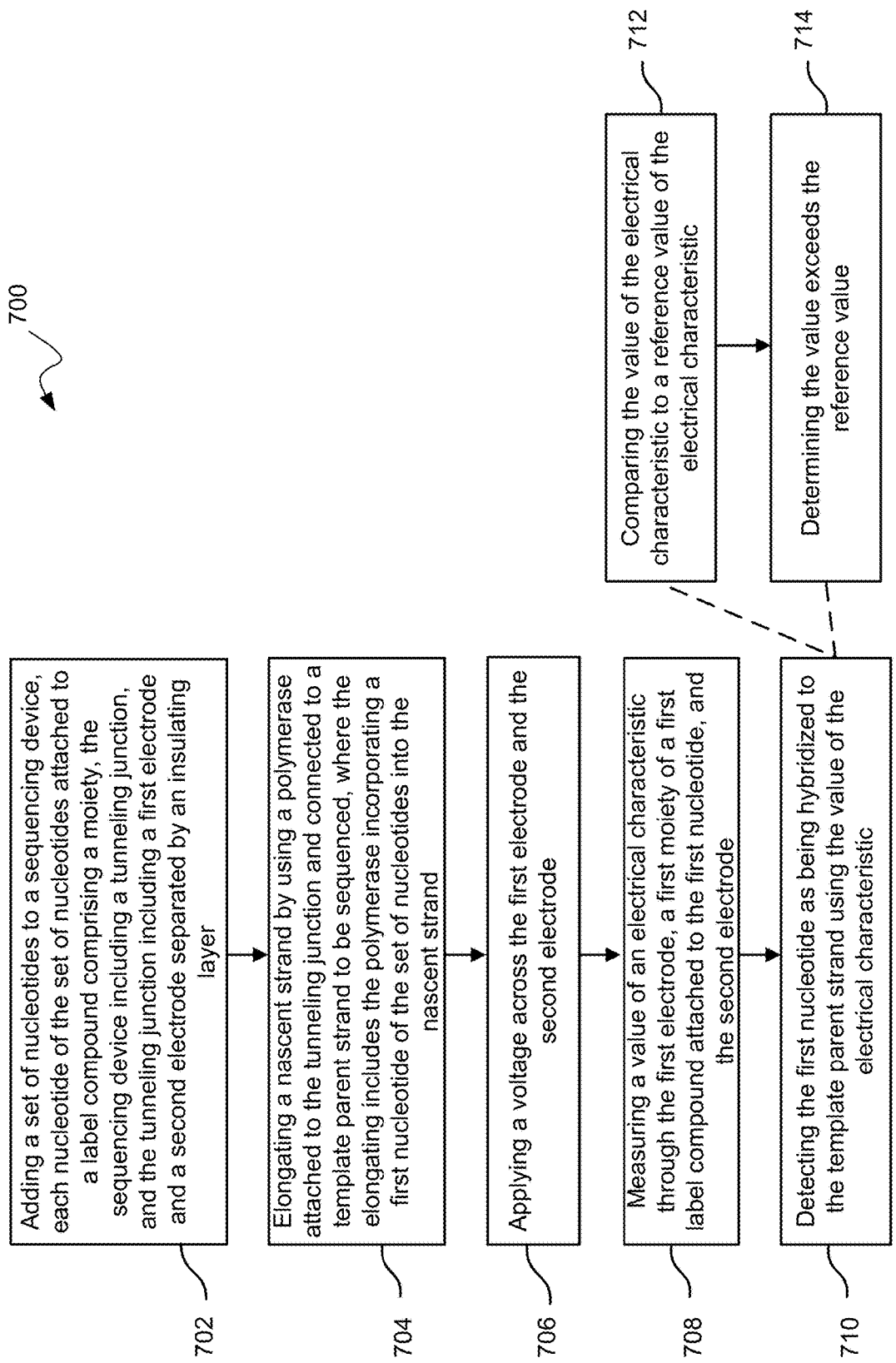
FIG. 7 illustrates steps of determining a nucleic acid sequence with an electrical tunneling junction according to embodiments of the present invention.

FIG. 7 shows a method 700 of determining a sequence of a nucleic acid using a sequencing device according to embodiments of the present technology. The sequencing device may include an electrical tunneling junction, a power supply, and a meter device. The tunneling junction includes a first electrode and a second electrode separated by an insulating layer.

Method 700 may include introducing a template parent strand to the tunneling junction. The template parent strand may be introduced to the tunneling junction with a fluid injection system. The template parent strand may be obtained from a biological sample.

At block 702, a set of nucleotides may be added to the sequencing device. Each nucleotide of the set of nucleotides may be attached to a label compound, with the label compound including a moiety. The set of nucleotides may be added to the sequencing device by including the set of nucleotides in a liquid that contacts the sequencing device. The liquid may be an ionic liquid. The moiety may be selected from the group consisting of an organometallic compound, a nanoparticle, and a conjugated aromatic, or may be any moiety described herein. Each nucleotide of the set of nucleotides may be attached to a respective label compound including a respective moiety. In some embodiments, each nucleotide of the set of nucleotides may be the same type of nucleotide. For example, each nucleotide of the set of nucleotides may be G nucleotides. Each moiety of each label compound may be the same type of moiety. In other embodiments, the set of nucleotides may include two, three, or four types of nucleotides. In these embodiments, each nucleotide may be attached to a different type of moiety. The liquid with the set of nucleotides may be stored in a reservoir and introduced by an injection system to the tunneling junction.

At block 704, a nascent strand may be elongated by a polymerase attached to the tunneling junction and connected to a template parent strand to be sequenced. A nascent strand may be a single-stranded nucleic acid molecule. Elongating the strand may include incorporating a first nucleotide of the set of nucleotides into the nascent strand via hybridization to the template parent strand. Together, the nascent strand and the template parent strand may form a portion of a double-stranded nucleic acid molecule.

The label compound may include a terminator configured to prevent further elongation of the nascent strand. A problem with conventional tunneling junctions in sequencing may be that a molecule to be analyzed may flow past the junction too quickly, making contact with the electrode for a short duration. The current signal may then be too short and difficult to characterize. In addition, even if only one type of nucleotide is added in block 704, a particular sequence in the template parent strand may include the same type of nucleotide multiple times and consecutively. The nucleic acid molecule may then add multiple nucleotides of the same type from a single introduction. As a result, the device may generate only one signal for one nucleotide when multiple nucleotides have been added. The terminator may stop polymerase action until the terminator is removed. In this manner, only one nucleotide may be added at a time, allowing enough time for a current signal to be measured.

The set of nucleotides except the first nucleotide may be removed from contacting the tunneling junction. Removing the nucleotides may include rinsing the tunneling junction with water. The liquid used to rinse the tunneling junction may be water or an ionic liquid without a nucleotide. This rinse liquid may be stored in a reservoir and introduced to the tunneling junction with an injection system. Removing the set of nucleotides may occur before measuring a value of the electrical characteristic. In other embodiments, the set of nucleotides may not be removed before measuring the value of the electrical characteristic.

At block 706, a voltage may be applied across the first electrode and the second electrode of the sequencing device. The voltage may be any voltage suitable to generate a tunneling current through an entity that contacts the tunneling junction. The voltage may be applied after removing the set of nucleotides except for the first nucleotide (e.g., after rinsing). In some embodiments, the voltage may be applied for a longer duration, including before the rinse, during elongation (e.g., block 704), or during addition of the set of nucleotides (block 702). In some embodiments, a constant voltage may be applied throughout the method.

At block 708, a value of an electrical characteristic through the first electrode, the moiety, and the second electrode may be measured. The electrical characteristic may be current, voltage, resistance, inductance, or pulse width. The value may be an average (mean, median, mode, root mean squared), a local or global maximum, or an instantaneous measurement. The value may be greater than 10 nA, greater than 100 nA, or greater than 1 $\mu$A.

At block 710, the first nucleotide may be detected as being hybridized to the template parent strand using the value of the electrical characteristic. Blocks 712 and 714 describe how the first nucleotide may be detected.

At block 712, the value of the electrical characteristic may be compared to a reference value of the electrical characteristic. The reference value may be of a background tunneling current that is through the first electrode and the second electrode and that does not pass through the moiety. The reference value may be based on a background tunneling current. For example, the reference value may be set at a maximum level of the background tunneling current or set at a value that would be statistically different from a background electrical characteristic. For example, the reference value may be set at one, two, or three standard deviations from an average background tunneling current. In some embodiments, the reference value may be zero.

At block 714, the value may be determined to exceed the reference value. For example, the value may be determined to be greater than the background tunneling current. The current signal may be transformed into a binary signal of 1 when the value is determined to exceed the reference value.

Method 700 may include cleaving the first label compound from the first nucleotide. Cleaving the first label compound removes a terminator, which allows the polymerase to elongate the nascent strand with additional nucleotides. Cleaving the first label compound may with photocleavage, which may include flashing a light at a certain wavelength or range of wavelengths to affect a photosensitive portion of the first label compound. In some embodiments, cleaving the first label compound may include chemically cleaving by introducing a cleaving agent, which may include a pH-adjusting agent (e.g., an acid or base), an enzyme, or a chemical reagent. In some embodiments, cleaving may be metal (e.g., palladium) catalyzed, reductive, oxidative, nucleophilic, or electrophilic.

1. Repeated Measurements With Another Nucleotide

Method 700 may further include repeating measurement and detection with another nucleotide after cleaving the first label compound. Method 700 may include a second set of nucleotides being added the sequencing device. Each nucleotide of the second set of nucleotides is attached to a second label compound including a second moiety. Each nucleotide of the second set of nucleotides being a different type of nucleotide than the first nucleotide. Each second label compound may be the same as the first label compound. Each second moiety may be the same type of moiety as the first moiety.

After the nascent strand is elongated by incorporating the first nucleotide, the nascent strand may become an elongated nascent strand (i.e., the nascent strand with the addition of the first nucleotide). Method 700 may include further elongating the elongated nascent strand by the polymerase. The acid polymerase may incorporate a second nucleotide of the second set of nucleotides attached to the second label compound, which includes the second moiety.

A second value of the electrical characteristic through the first electrode, the second moiety, and the second electrode may be measured. Based on the second value of the electrical characteristic, the second nucleotide may be detected as being hybridized to the template parent strand. The measurement and detection may be the same as any measurement and detection described for the first nucleotide. In embodiments where the polymerase does not incorporate the second nucleotide or any nucleotide of the second set of nucleotides, the second value of the electrical characteristic may be determined as statistically equivalent to the reference value, and the absence of an additional nucleotide would be determined.

2. Multiple Types of Nucleotides in the Set of Nucleotides

In some embodiments, the set of nucleotides added in block 704 may include two or more types of nucleotides. The set of nucleotides may include a second nucleotide attached to a second label compound including a second moiety. Detecting the first nucleotide as being hybridized in block 710 may include comparing the value of the electrical characteristic in block 712. In method 700, the second nucleotide may be determined as not being hybridized to the template strand based on the value of the electrical characteristic by comparing the value of the electrical characteristic to a second reference value of the electrical characteristic. The second reference value may have a same value or a different value than the first reference value.

The first moiety may generate a value of an electrical characteristic in a certain range or above or below a certain value. The second moiety may generate a value of an electrical characteristic in a different range or above or below a certain value. The measured value of the electrical characteristic may be compared to the different ranges or values to determine which moiety, and therefore which nucleotide, is indicated by the value of the electrical characteristic. The first reference value and the second reference value may be an endpoint in ranges of values for the first moiety or the second moiety.

3. Multiple Tunneling Junctions

Method 700 may include determining a sequence of a nucleic acid using a plurality of tunneling junctions. Each tunneling junction may include a respective first electrode, a respective second electrode, and a respective insulating layer. Each respective tunneling junction is attached to a respective polymerase.

Method 700 may include steps for each tunneling junction of the plurality of tunneling junctions. A respective voltage may be applied across the respective first electrode and the respective second electrode. A respective nascent strand may be elongated using the respective polymerase attached to the respective tunneling junction and connected to a respective parent strand to be sequenced. Elongating may include the respective polymerase incorporating the respective nucleotide of the set of nucleotides into the respective nascent strand via hybridization to the respective template parent strand. A respective value of the electrical characteristic may be measured through the respective first electrode, the respective moiety of a respective label compound attached to the respective nucleotide, and the respective second electrode. The respective nucleotide may be detected as being hybridized to the respective template parent strand using the respective value of the electrical characteristic.

Each tunneling junction of the plurality of tunneling junctions may determine the presence or absence of a nucleotide being hybridized to the template parent strand. The plurality of junctions may number in the thousands, millions, or billions in a single device, which may be about a square centimeter. Because the detection involves identifying a binary signal of a 0 or 1, the read times for the tunneling junctions may be similar to that in a flash drive. Based on a flash drive, the read time for the tunneling junctions can be 80 megabits/sec (i.e., about 80 million junctions per second) to 5 gigabits/sec (i.e., about 5 billion junctions per second) or even faster. With tens of billions of tunneling junctions, the read time of all the tunneling junctions may be on the order of seconds. The wash cycle for the tunneling junctions may be on the order of 100 µs, less than the read time.

In embodiments, the first set of nucleotides is removed before the second set of nucleotides is added. In other embodiments the first set of nucleotides may not be removed (e.g., by a rinsing step) before the second set of nucleotides is added. In this manner, the second nucleotide may be hybridized to parent template strands at certain tunneling junctions. The total number of tunneling junctions with a current signal would be from any parent strands that have either a nucleotide from the first set of nucleotides or a nucleotide from the second set of nucleotides. Because the addition of nucleotides is done sequentially, the junctions with a nucleotide from the second set of nucleotides can be deduced based on the signals that did not appear with addition of the first set of nucleotides. This process can be then repeated with the remaining nucleotides. The wash can then be done after the multiple sets of nucleotides are introduced.

In some embodiments, with a plurality of tunneling junctions, two different types of nucleotides may be introduced at a time instead of a single nucleotide. A measurement may be made to see which tunneling junctions have included any of the two different types of nucleotides with two different label compounds. A first type of the nucleotide is then removed with a nucleotide-specific removal process. For example, label compounds with the first type of nucleotide may be removed with a certain wavelength of light, while the label compounds with the second type of nucleotide may not be removed from the nascent strand. After the removal, another measurement is made to identify tunneling junctions with the second type of nucleotide. As a result of this technique, the tunneling junctions that incorporated the first type of nucleotide, and the tunneling junctions that incorporated the second type of nucleotide can be determined. This technique may also be used for more than two types of nucleotides, so long as the label compounds for the types of nucleotides can be selectively removed.

Method 700 may be adapted for analyzing molecules other than nucleic acid sequences. For example, if a protein is to be analyzed for the amino acid sequence, the polymerase may be replaced by a ribosome. The amino acid would be labeled instead of the nucleotide. Depending on the molecule to be analyzed, the polymerase may also be replaced by a helicase, an exonuclease, along with other enzymes.

C. Magnetic Tunneling Junction Configurations

Figure 8:
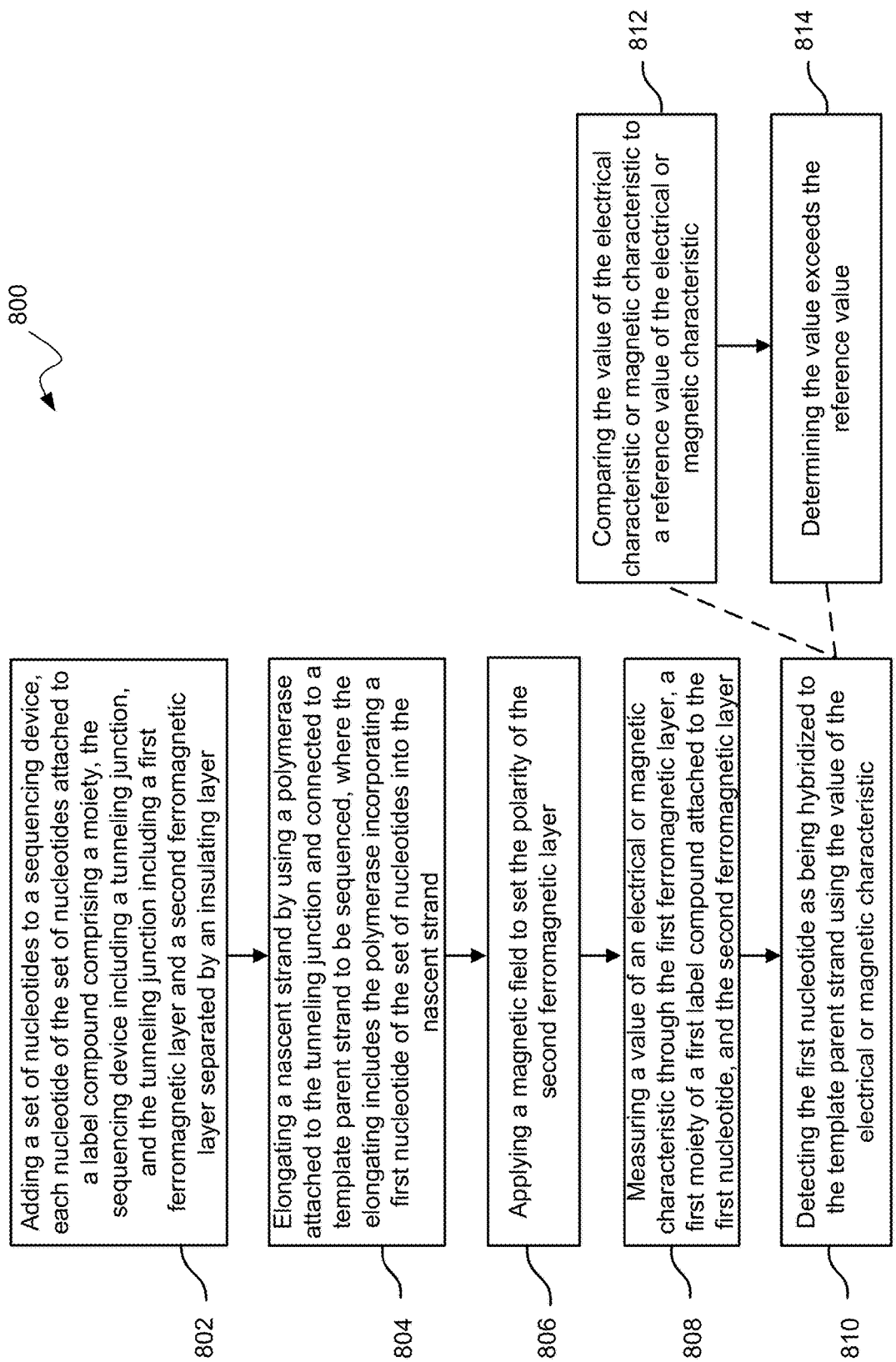
FIG. 8 illustrates steps of determining a nucleic acid sequence with a magnetic tunneling junction according to embodiments of the present invention.

FIG. 8 shows a method 800 of determining a sequence of a nucleic acid using a sequencing device according to embodiments of the present technology. The sequencing device may include a magnetic tunneling junction, a power supply, and a meter device. The tunneling junction includes a first ferromagnetic layer and a second ferromagnetic layer separated by an insulating layer. The ferromagnetic layer and the second ferromagnetic layer are examples of conductors described for tunneling junctions.

Method 800 may include introducing a template parent strand to the tunneling junction. The template parent strand may be introduced to the tunneling junction with a fluid injection system. The template parent strand may be obtained from a biological sample.

At block 802, a set of nucleotides may be added to the sequencing device. Each nucleotide of the set of nucleotides may be attached to a label compound, with the label compound including a moiety. The set of nucleotides may be added to the sequencing device by including the set of nucleotides in a liquid that contacts the sequencing device. The liquid may be an ionic liquid. The moiety may be selected from the group consisting of a ferromagnetic or superparamagnetic material. The material may include a magnetic nanoparticle (e.g., FePt, FeCuPt, $Fe_2O_3$) or may be any moiety described herein. Each nucleotide of the set of nucleotides may be attached to a respective label compound including a respective moiety. In some embodiments, each nucleotide of the set of nucleotides may be the same type of nucleotide. For example, each nucleotide of the set of nucleotides may be G nucleotides. Each moiety of each label compound may be the same type of moiety. In other embodiments, the set of nucleotides may include two, three, or four types of nucleotides. In these embodiments, each nucleotide may be attached to a different type of moiety. The liquid with the set of nucleotides may be stored in a reservoir and introduced by an injection system to the tunneling junction.

At block 804, a nascent strand may be elongated by a polymerase attached to the tunneling junction and connected to a template parent strand to be sequenced. A nascent strand may be a single-stranded nucleic acid molecule. Elongating the strand may include incorporating a first nucleotide of the set of nucleotides into the nascent strand via hybridization to the template parent strand. Together, the nascent strand and the template parent strand may form a portion of a double-stranded nucleic acid molecule.

The label compound may include a terminator configured to prevent further elongation of the nascent strand. Similar to the label compound used with electrical tunneling junctions, the label compound used with magnetic tunneling junctions is configured to allow for a longer signal by including a terminator.

The set of nucleotides except the first nucleotide may be removed from contacting the tunneling junction. Removing the nucleotides may include rinsing the tunneling junction with water. The liquid used to rinse the tunneling junction may be water or an ionic liquid without a nucleotide. This rinse liquid may be stored in a reservoir and introduced to the tunneling junction with an injection system. Removing the set of nucleotides may occur before measuring a value of the electrical characteristic. In other embodiments, the set of nucleotides may not be removed before measuring the value of the electrical characteristic.

At block 806, a magnetic field may be applied to set the polarity of the second ferromagnetic layer. The first ferromagnetic layer may be a permanent magnet and may have a first polarity. The magnetic field may be applied to the second ferromagnetic layer to set the polarity at a second polarity that is anti-parallel to the first polarity. The magnetic field may be applied by an external magnet. The magnetic field may be applied after removing the set of nucleotides except for the first nucleotide (e.g., after rinsing). In some embodiments, the voltage may be applied for a longer duration, including before the rinse, during elongation (e.g., block 804), or during addition of the set of nucleotides (block 802). In some embodiments, a constant magnetic field may be applied throughout the method.

At block 808, a value of an electrical or magnetic characteristic through the first ferromagnetic layer, the moiety, and the second ferromagnetic layer may be measured. The electrical characteristic may be current, voltage, resistance, inductance, or pulse width. The value may be an average (mean, median, mode, root mean squared), a local or global maximum, or an instantaneous measurement. The value may be greater than 10 nA, greater than 100 nA, or greater than 1 µA. The magnetic characteristic may be a magnetic field perturbation caused by magnetic nanoparticles and measured by magnetic sensors.

At block 810, the first nucleotide may be detected as being hybridized to the template parent strand using the value of the electrical or magnetic characteristic. Blocks 812 and 814 describe how the first nucleotide may be detected.

At block 812, the value of the electrical or magnetic characteristic may be compared to a reference value of the electrical or magnetic characteristic. The reference value may be of a background tunneling current, resistance, or other electrical characteristic that is through the first ferromagnetic layer and the second ferromagnetic layer and that does not pass through the moiety. The reference value may be based on a background tunneling current. For example, the reference value may be set at a maximum level of the background tunneling current or set at a value that would be statistically different from a background electrical characteristic. For example, the reference value may be set at one, two, or three standard deviations from an average background tunneling current. In some embodiments, the reference value may be zero.

At block 814, the value may be determined to exceed the reference value. For example, the value may be determined to be greater than the background tunneling current. The current signal may be transformed into a binary signal of 1 when the value is determined to exceed the reference value.

Method 800 may include cleaving the first label compound from the first nucleotide. Cleaving the first label compound removes a terminator, which allows the polymerase to elongate the nascent strand with additional nucleotides. Cleaving the first label compound may with photocleavage, which may include flashing a light at a certain wavelength or range of wavelengths to affect a photosensitive portion of the first label compound. In some embodiments, cleaving the first label compound may include chemically cleaving by introducing a cleaving agent, which may include a pH-adjusting agent (e.g., an acid or base), an enzyme, or a chemical reagent. In some embodiments, cleaving may be metal (e.g., palladium) catalyzed, reductive, oxidative, nucleophilic, or electrophilic.

Method 800 may include repeated measurements with another nucleotide, multiple types of nucleotides in the set of nucleotides, and/or multiple tunneling junctions similar to what has been described for electrical tunneling junctions. Similar to method 700, method 800 may be adapted for analyzing molecules other than nucleic acid sequences.

IV. ANALYSIS SYSTEM

Methods to determine the sequence of a nucleic acid may including using a system with a tunneling junction. The tunneling junction may include a first conductor and a second conductor, separated by an insulating layer. The conductors may be electrodes or ferromagnetic layers. A polymerase may be attached to the junction and connected to a template parent strand. The polymerase may be configured to elongate a nascent strand that is hybridized to the template parent strand. A power supply may be in electrical communication with at least one of the first conductor and the second conductor. The system may include a set of nucleotides. Each nucleotide of the set of nucleotides may be attached to a label compound. The label compound may include a moiety. The system may further include a meter device configured to measure a value of an electrical characteristic through the first conductor and the second conductor via the moiety.

The system may include a computer readable medium storing a plurality of instructions. The plurality of instructions, when executed by a processor, may cause the processor to measure the value of the electrical characteristic through the first conductor and the second conductor. The instructions may also cause the processor to compare the value of the electrical characteristic to a reference value of the electrical characteristic. Upon determining the value exceeds the reference value, the instructions may cause the processor to detect a nucleotide as being hybridized to the template parent strand.

Systems specific to electrical tunneling junctions and magnetic tunneling junctions are described below.

A. Electrical Tunneling Junction Systems

Figure 9:
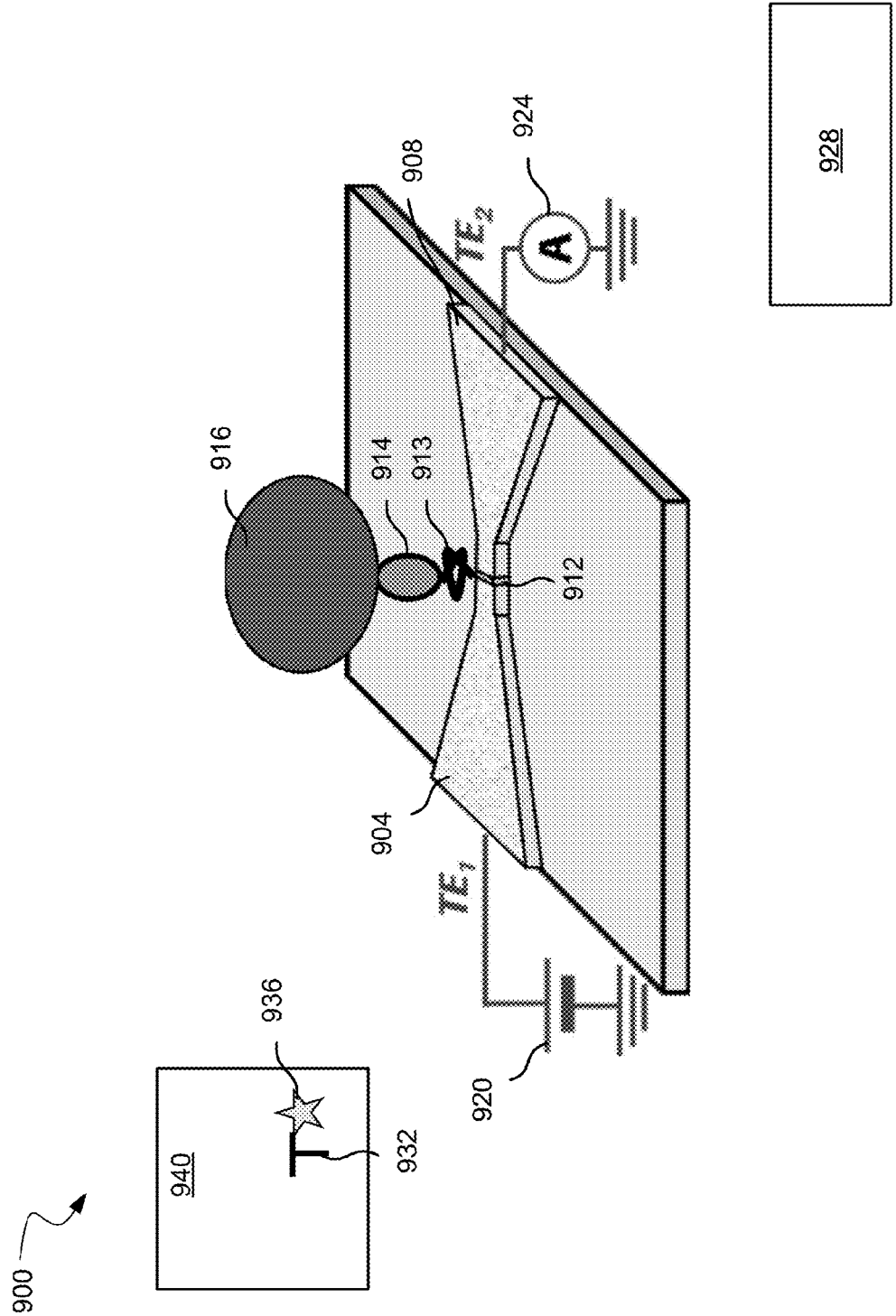
FIG. 9 shows an example system with an electrical tunneling junction according to embodiments of the present invention.

FIG. 9 shows an example system 900. System 900 may include a tunneling junction. Tunneling junction includes a first electrode 904, a second electrode 908, and an insulating layer 912. The electrode materials may include gold, silver, platinum, or palladium. The electrode may include any metal that has a metal oxide that is chemically stable in the aqueous solution used as the medium for the molecule to be analyzed. Other metals may include tantalum, nickel, chrome, titanium, and copper.

Insulating layer 912 may include a dielectric material, including alumina ($Al_2O_3$), hafnia ($HfO_2$), silicon nitride ($Si_3N_4$), silicon oxide ($SiO_2$), glass, quartz, magnesium oxide (MgO), titanium dioxide ($TiO_2$), or zirconium dioxide ($ZrO_2$). Insulating layer 912 may have a thickness greater than 2 nm. The thickness may be the distance between first electrode 904 and second electrode 908. Because operation of the tunnel junction does not require the nucleotide or nucleotides of a nucleic acid molecule to contact both electrodes, the width of the insulating layer may be greater than the size of a nucleotide or nucleotides. In addition, the width of the insulating layer may be larger than the size of the moiety as tunneling may still occur even if the moiety is smaller than the gap between the electrodes.

The tunneling junction may be oriented laterally, such that the tunneling direction is substantially parallel to the surface of a substrate contacting the first electrode and the second electrode. The direction of the elongation of the nascent strand may be parallel to the surface of the substrate. The insulating layer may have a longitudinal axis that is orthogonal to the substrate. Examples of laterally-oriented tunneling junctions are described in U.S. Patent Publication No. 2018/0031523 A1, the contents of which are incorporated herein by reference for all purposes.

A nucleic acid polymerase 916 may be attached to the tunneling junction by a tether compound formed by tether compound 913 and compound 914. Tether compound 913 may include SpyTag, and compound 914 may include SpyCatcher. Nucleic acid polymerase 916 may be attached to the tunneling junction at insulating layer 912. Nucleic acid polymerase 916 may also be attached to the tunneling junction at first electrode 904 or second electrode 908. Nucleic acid polymerase 916 may be configured to add a nucleotide as described in FIG. 6 with configuration 640. A compound or compounds may tether nucleic acid polymerase 916 to insulating layer 912. For example, hydroquinone, SpyTag, or SpyCatcher may be used to tether nucleic acid polymerase 916 to insulating layer 912. Nucleic acid polymerase 916 may be configured to elongate a nascent strand. The nascent strand may be hybridized to a template parent strand.

System 900 may include a power supply 920. Power supply 920 may be in electrical communication with at least one of first electrode 904 and second electrode 908. Power supply 920 may apply a voltage to first electrode 904 and second electrode 980. Power supply 920 may be configured to maintain a desired current or a desired voltage. Power supply 920 may provide voltages from 0 to 1 V, including from 10 mV to 100 mV, from 100 mV to 200 mV, from 200 mV to 300 mV, from 300 mV to 500 mV, or from 500 mV to 1 V. In some embodiments, power supply 920 may provide currents of 0 to 30 nA, including from 1 pA to 10 pA, from 10 pA to 100 pA, from 100 pA to 1 nA, 1 nA to 10 nA, or from 10 nA to 30 nA.

System 900 may also include a meter device 924. Meter device 924 may be configured to measure a value of an electrical characteristic through first electrode 904 and second electrode 908. Meter device 924 may be a current meter, a voltage meter, or an oscilloscope. The electrical characteristic may be current or voltage.

System 900 may include a computer system 930. Computer system 928 may be in communication with power supply 920 and meter device 924. Computer system 928 may also be in communication with control systems that deliver fluid to the tunneling junction. Computer system 928 may include a processor and a computer readable medium. The computer readable medium may be store a plurality of instructions. The plurality of instructions, when executed by a process, may cause the processor to perform any method described herein. For example, the plurality of instructions, when executed, may cause the processor to measure the value of the electrical characteristic through the first electrode and the second electrode. The processor may also be caused to compare the value of the electrical characteristic to a reference value of the electrical characteristic. Upon determining the value exceeds the reference value, the processor may further be caused to detect a nucleotide as being hybridized to the template parent strand. Upon determining the value does not exceed the reference value, the processor may further be caused to determine the absence of the nucleotide being hybridized to the template parent strand. Computer system 928 is described in greater detail below.

System 900 may include a nucleotide 932 attached to a label compound 936. Label compound 936 may include a moiety. Label compound 936 may be any label compound described herein. The moiety may be any moiety described herein.

System 900 may include a reservoir 940. Reservoir 940 may be in fluid communication with the tunneling junction. An injection system may be configured to deliver a liquid from reservoir 940 to the tunneling junction. Reservoir 940 may include nucleotide 932 attached to label compound 936. Reservoir 940 may include water. In some embodiments, system 900 may include a plurality of reservoirs. Each reservoir may include a different liquid to be injected to the tunneling junction. For example, a different reservoir may be used for each of the four types of nucleotide. An additional reservoir may be included to deliver water to rinse the nucleotides from the tunneling junction.

System 900 may include a plurality of tunneling junctions. The plurality of tunneling junctions may number in the thousands, millions, or billions per square centimeter. Each tunneling junction may be on the surface of the same substrate. The substrate may include a semiconductor wafer, including a silicon wafer or silicon-on-insulator wafer. Each tunneling junction may be fabricated using semiconductor processing techniques. Each tunneling junction may be identical. Power supply 920 may be in electrical communication with the plurality of tunneling junctions. Meter device 924 or a plurality of meter devices may be in electrical communication with the plurality of tunneling junctions.

B. Magnetic Tunneling Junction Systems

1. Single Magnetic Tunneling Junction

Figure 10:
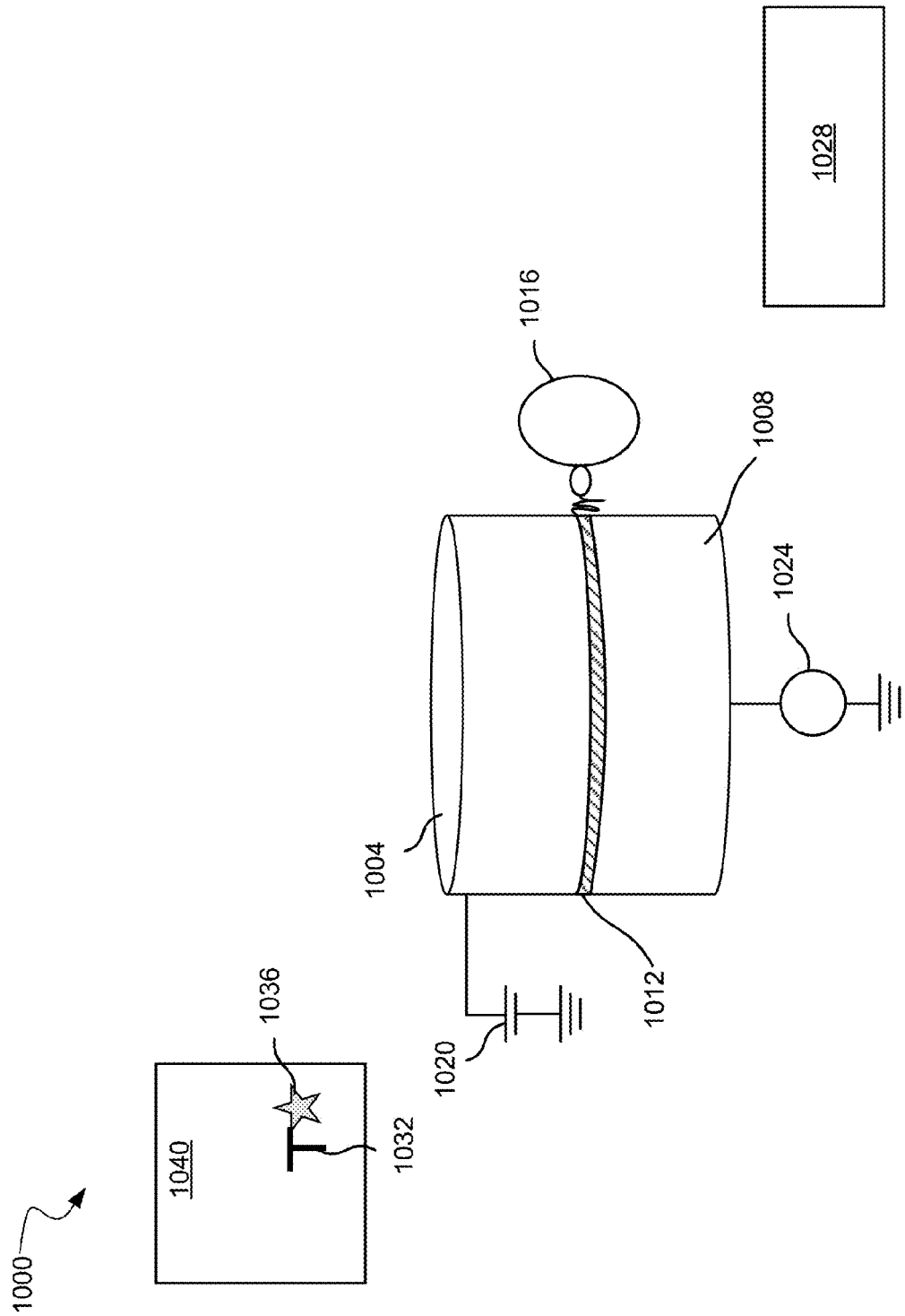
FIG. 10 shows an example system with a magnetic tunneling junction according to embodiments of the present invention.

FIG. 10 shows an example system 1000. System 1000 may include a tunneling junction. Tunneling junction includes a first ferromagnetic layer 1004, a second ferromagnetic layer 1008, and an insulating layer 1012. The material for the ferromagnetic layers may include cobalt; Co/I/La$_{2/3}$Sr$_{1/3}$MnO$_3$ (LSMO) where I is SrTiO$_3$ (STO), Ce$_{0.69}$La$_{0.31}$, or O$_{1.845}$ (CLO); CoGd; CoPt; CoFe; CoFeB; CoFeTb; iron; Fe$_2$O$_3$; FeOFe$_2$O$_3$; NiOFe$_2$O$_3$; CuOFe$_2$O$_3$; MgOFe$_2$O$_3$; MnBi; Ni; MnSb; MnOFe$_2$O$_3$; Y$_3$Fe$_5$O$_{12}$; MnAs; Gd; Tb; Dy; or EuO. The material for the two ferromagnetic layers may be the same or different. One ferromagnetic layer may be a permanent magnet with one polarity. The other ferromagnetic layer may have its polarity set by an applied magnetic field.

Insulating layer 1012 may include a dielectric material, including alumina (Al$_2$O$_3$), hafnia (HfO$_2$), silicon nitride (Si$_3$N$_4$), silicon oxide (SiO$_2$), glass, quartz, magnesium oxide (MgO), titanium dioxide (TiO$_2$), or zirconium dioxide (ZrO$_2$). Insulating layer 1012 may have a thickness greater than 2 nm. The thickness may be the distance between first ferromagnetic layer 1004 and second ferromagnetic layer 1008. Because operation of the tunnel junction does not require the nucleotide or nucleotides of a nucleic acid molecule to contact both ferromagnetic layers, the width of the insulating layer may be greater than the size of a nucleotide or nucleotides. In addition, the width of the insulating layer may be larger than the size of the moiety as tunneling may still occur even if the moiety is smaller than the gap between the ferromagnetic layers.

The tunneling junction may be oriented laterally, such that the tunneling direction is substantially parallel to the surface of a substrate contacting the first electrode and the second electrode. The direction of the elongation of the nascent strand may be parallel to the surface of the substrate. The insulating layer may have a longitudinal axis that is orthogonal to the substrate. Examples of laterally-oriented tunneling junctions are described in U.S. Patent Publication No. 2018/0031523 A1, the contents of which are incorporated herein by reference for all purposes.

A nucleic acid polymerase 1016 may be attached to the tunneling junction. Nucleic acid polymerase 1016 may be attached to the tunneling junction at insulating layer 1012. A compound or compounds may tether nucleic acid polymerase 1016 to insulating layer 1012. For example, hydroquinone, SpyTag, or SpyCatcher may be used to tether nucleic acid polymerase 1016 to insulating layer 1012. Nucleic acid polymerase 1016 may be configured to elongate a nascent strand. The nascent strand may be hybridized to a template parent strand.

However, nucleic acid polymerase 1016 may not be attached to the tunneling junction. A magnetic tunneling junction does not need a moiety to make contact with any portion of the tunneling junction, as magnetic fields from a moiety can travel through materials along with empty space. The magnetic tunneling junction may be embedded in a non-ferromagnetic material, which may be attached to nucleic acid polymerase 1016.

System 1000 may include a power supply 1020. Power supply 1020 may be in electrical communication with at least one of first ferromagnetic layer 1004 and second ferromagnetic layer 1008. Power supply 1020 may apply a voltage to first ferromagnetic layer 1004 and second ferromagnetic layer 1008. Power supply 1020 may be configured to maintain a desired current or a desired voltage. Power supply 1020 may provide voltages from 0 to 3 V, including from 10 mV to 100 mV, from 100 mV to 200 mV, from 200 mV to 300 mV, from 300 mV to 500 mV, from 500 mV to 1 V, from 1 V to 2 V, or from 2 V to 3 V. In some embodiments, power supply 1020 may provide currents of 0 to 10 µA, including from 1 pA to 10 pA, from 10 pA to 100 pA, from 100 pA to 1 nA, 1 nA to 10 nA, from 10 nA to 30 nA, from 30 nA to 100 nA, from 100 nA to 500 nA, from 500 nA to 1 µA, or from 1 µA to 10 µA.

System 1000 may also include a meter device 1024. Meter device 1024 may be configured to measure a value of an electrical or magnetic characteristic through first ferromagnetic layer 1004 and second ferromagnetic layer 1008. Meter device 1024 may be a current meter, a voltage meter, or an oscilloscope. The electrical characteristic may be current or voltage. Meter device 1024 may be a magnetic sensor to measure a magnetic field.

System 1000 may include a computer system 1028. Computer system 1028 may be in communication with power supply 1020 and meter device 1024. Computer system 1028 may also be in communication with control systems that deliver fluid to the tunneling junction. Computer system 1028 may include a processor and a computer readable medium. The computer readable medium may be store a plurality of instructions. The plurality of instructions, when executed by a process, may cause the processor to perform any method described herein. For example, the plurality of instructions, when executed, may cause the processor to measure the value of the electrical characteristic through the first ferromagnetic layer and the second ferromagnetic layer. The processor may also be caused to compare the value of the electrical characteristic to a reference value of the electrical characteristic. Upon determining the value exceeds the reference value, the processor may further be caused to detect a nucleotide as being hybridized to the template parent strand. Upon determining the value does not exceed the reference value, the processor may further be caused to determine the absence of the nucleotide being hybridized to the template parent strand. Computer system 1028 is described in greater detail below.

System 1000 may include a nucleotide 1032 attached to a label compound 1036. Label compound 1036 may include a moiety. Label compound 1036 may be any label compound described herein. The moiety may be any moiety described herein.

System 1000 may include a reservoir 1040. Reservoir 1040 may be in fluid communication with the tunneling junction. An injection system may be configured to deliver a liquid from reservoir 1040 to the tunneling junction. Reservoir 1040 may include nucleotide 1032 attached to label compound 1036. Reservoir 1040 may include water. In some embodiments, system 1000 may include a plurality of reservoirs. Each reservoir may include a different liquid to be injected to the tunneling junction. For example, a different reservoir may be used for each of the four types of nucleotide. An additional reservoir may be included to deliver water to rinse the nucleotides from the tunneling junction.

2. Multiple Tunneling Junctions

System 1000 may include a plurality of tunneling junctions. The plurality of tunneling junctions may number in the thousands, millions, or billions per square centimeter. Each tunneling junction may be on the surface of the same substrate. The substrate may include a semiconductor wafer, including a silicon wafer or silicon-on-insulator wafer. Each tunneling junction may be fabricated using semiconductor processing techniques. Each tunneling junction may be identical. Power supply 1020 may be in electrical communication with the plurality of tunneling junctions. Meter device 1024 or a plurality of meter devices may be in electrical communication with the plurality of tunneling junctions.

Figure 11:
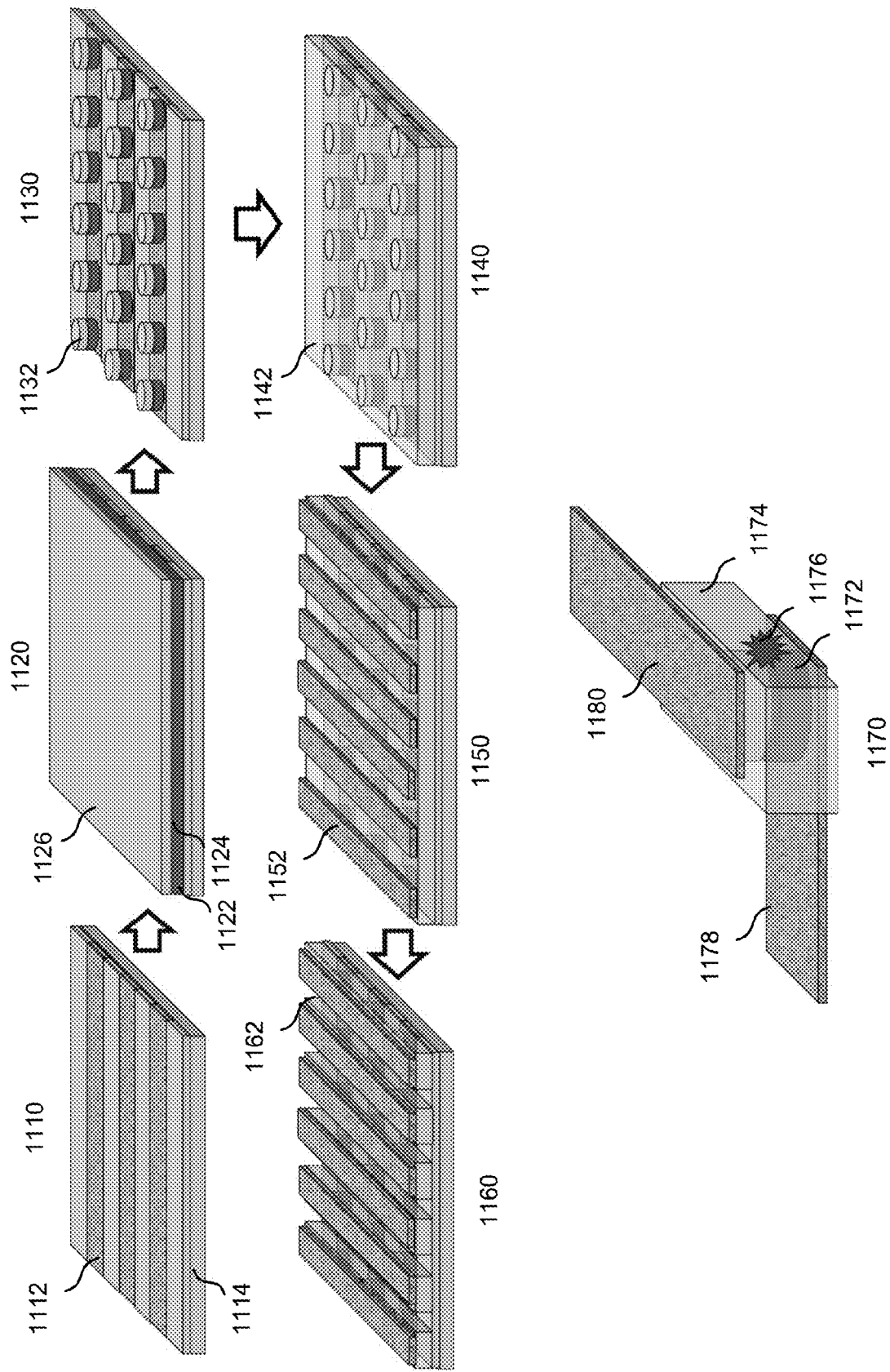
FIG. 11 shows processing stages for fabricating a plurality of magnetic tunneling junctions according to embodiments of the present invention.

FIG. 11 shows processing stages for fabricating a plurality of magnetic tunneling junctions. At stage 1110, a conducting material deposited and patterned into line 1112 on substrate 1114. In the completed device, line 1112 may be analogous to a word line or a bit line in conventional memory systems.

At stage 1120, first ferromagnetic material 1122, insulating material 1124, and second ferromagnetic material 1126 are deposited as layers on top of line 1112.

At stage 1130, first ferromagnetic material 1122, insulating material 1124, and second ferromagnetic material 1126 are patterned to form a plurality of tunneling junctions, including tunneling junction 1132. Tunneling junction 1132 is shown as cylindrical in shape. However, tunneling junction 1132 may include other shapes, including a rectangular solid, a cube, or a cone.

At stage 1140, insulating material 1142 is deposited. Insulating material 1142 may be deposited to the same height as tunneling junction 1132. Insulating material 1142 may fill the space between tunneling junctions, while leaving second ferromagnetic material 1126 exposed.

At stage 1150, a conducting material deposited and patterned into line 1152 on insulating material 1142. Line 1152 contacts second ferromagnetic material 1126 of the plurality of tunneling junctions. Line 1152 may be analogous to a word line or a bit line in conventional memory systems, with line 1152 being the other type of line as line 1112.

At stage 1160, insulating material 1142 is patterned to expose line 1112. The patterning forms a channel 1162 defined by line 1152 and insulating material 1142 under line 1152. Channel 1162 may facilitate flow of nucleotides and fluid to the tunneling junctions.

Diagram 1170 shows an enlarged view of a tunneling junction 1172. Tunneling junction 1172 may be embedded within a block of insulating material 1174. Tunneling junction 1172 may generate a tunneling current above a reference value when a moiety 1176 is near tunneling junction 1172, but moiety 1176 does not contact tunneling junction 1172. Moiety 1176 may contact insulating material 1174. Line 1178 and line 1180 can be used to detect a tunneling current through tunneling junction 1172.

V. EXAMPLES

A. Fabricating Vertical Electrical Tunneling Junctions

Vertical electrical tunneling junctions were fabricated to test tunneling current with different thicknesses of the insulating layers, different insulating materials, and different applied voltages.

Figure 12:
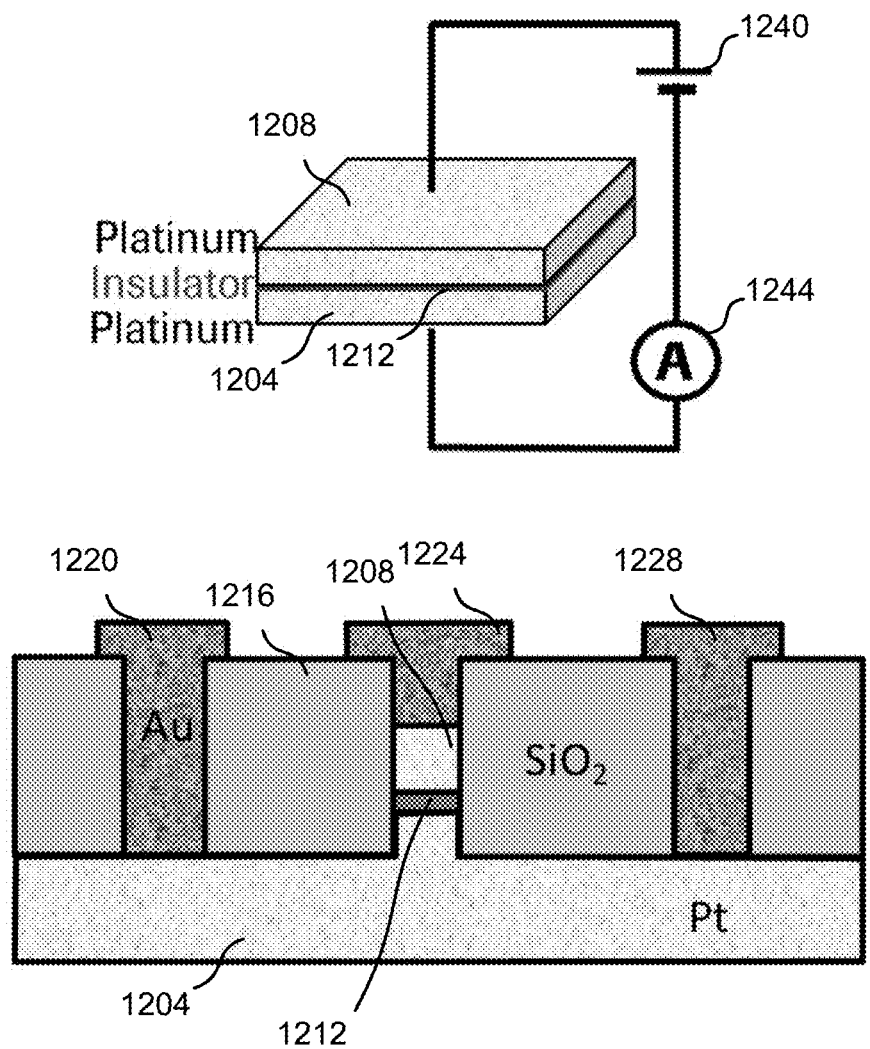
FIG. 12 shows the configuration of a fabricated vertical electrical tunneling junction according to embodiments of the present invention.

FIG. 12 shows the configuration of a fabricated vertical electrical tunneling junction used for materials characterization. The tunneling junction is a first platinum layer 1204 and a second platinum layer 1208 separated by an insulating layer 1212. The material for insulating layer 1212 is alumina ($Al_2O_3$), hafnia ($HfO_2$), or magnesium oxide (MgO).

Silicon dioxide 1216 is deposited and patterned to electrically isolate contacts 1220, 1224, and 1228. Contacts 1220, 1224, and 1228 are gold. A tunneling junction may be connected to a power source 1240 and a current meter 1244.

B. Electrical Results From Vertical Electrical Tunneling Junctions.

Figure 13A:
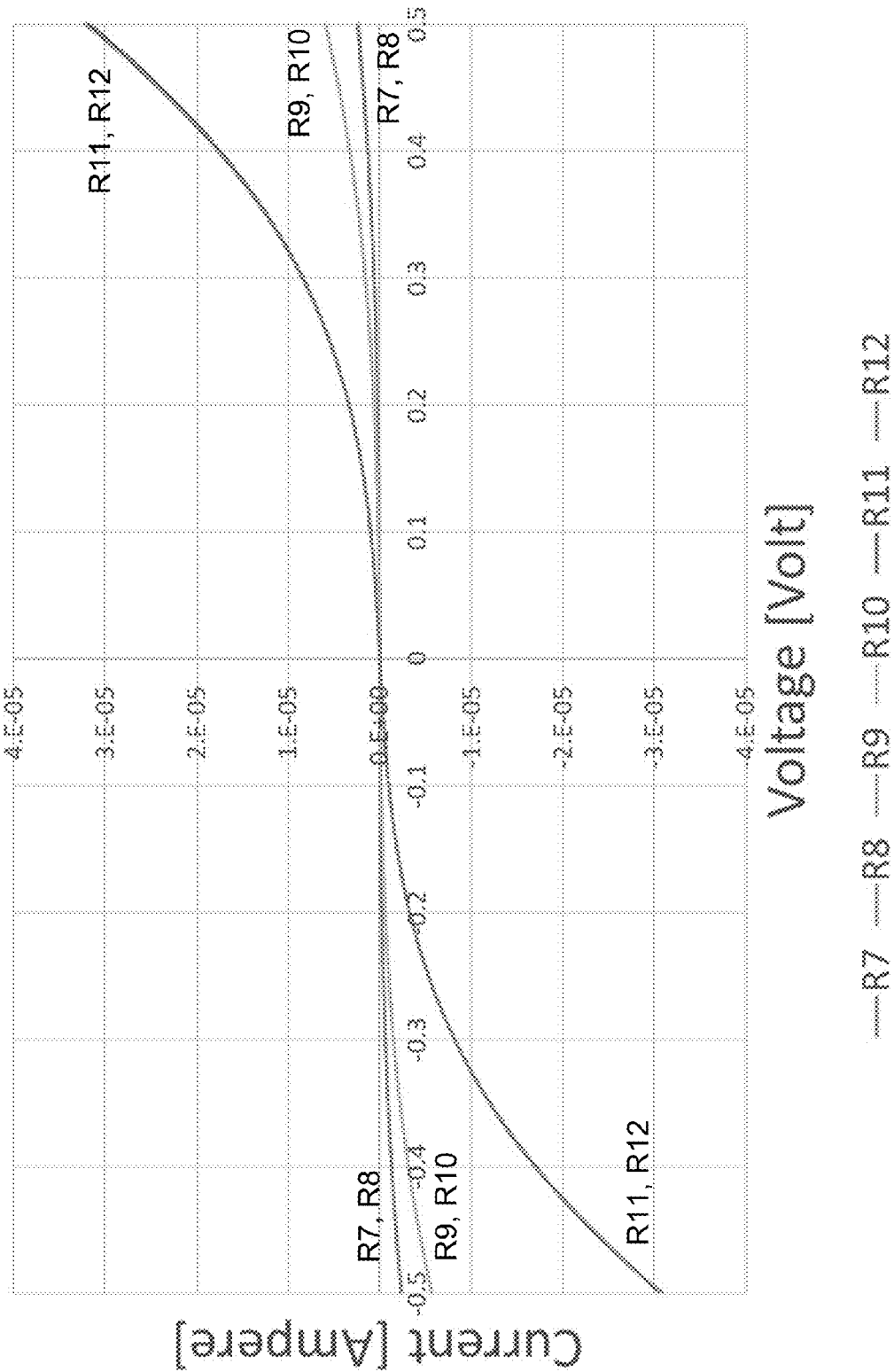
FIGS. 13A and 13B show electrical results from testing vertical tunneling junctions according to embodiments of the present invention.
Figure 13B:
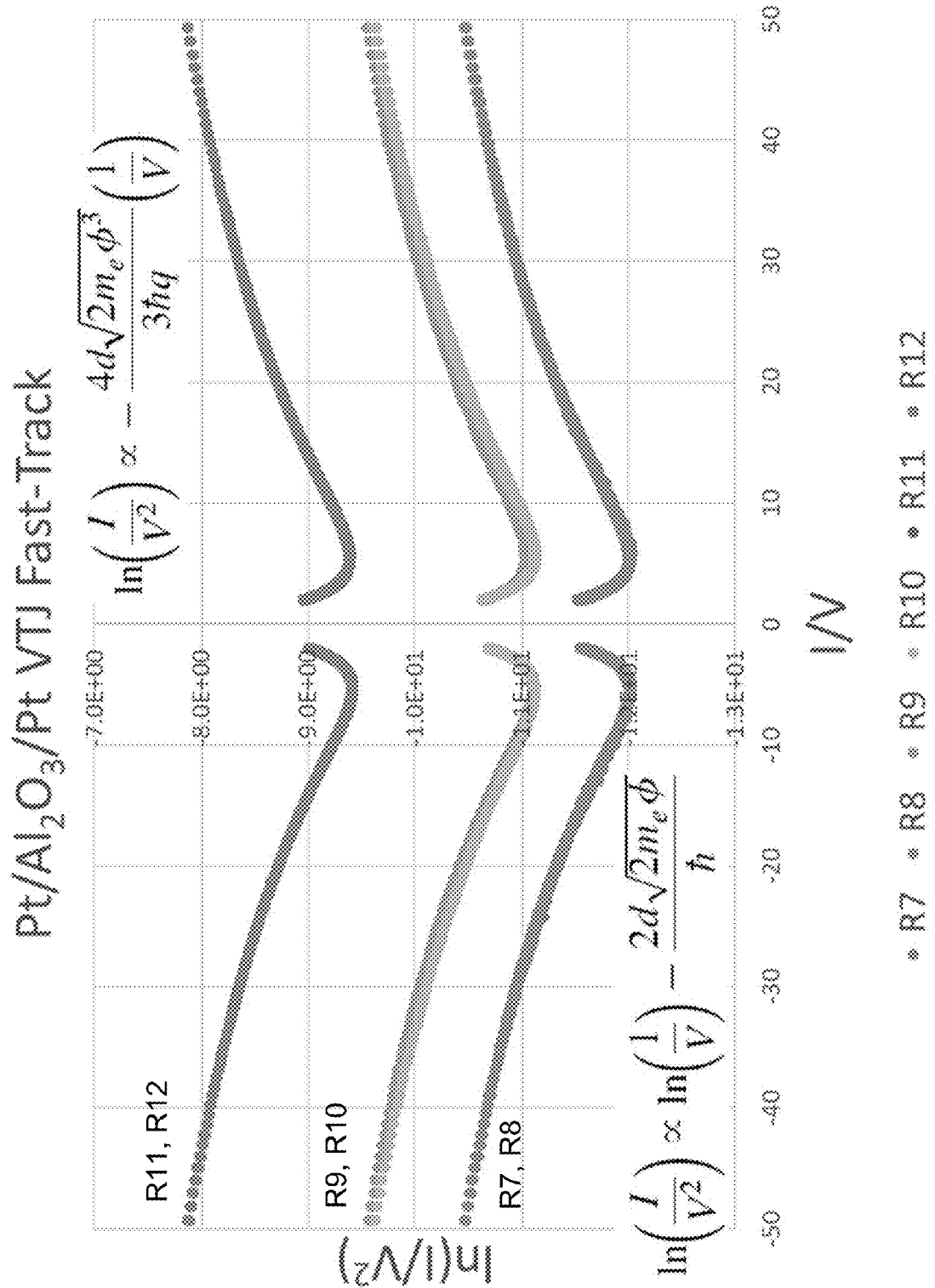

FIGS. 13A and 13B show electrical results from testing vertical tunneling junctions with a configuration similar to that illustrated in FIG. 12. The vertical tunneling junctions are fabricated to be circular rather than square. R7 and R8 refer to devices with a 500 nm junction diameter. R9 and R10 refer to devices with a 750 nm junction diameter. R11 and R12 refer to devices with a 1 μm junction diameter. FIG. 13A shows the current versus voltage for the devices. The devices show rectifying behavior indicating electron transport by tunneling. FIG. 13B shows the natural logarithm of the quantity of the current divided by the voltage squared versus the current divided by the voltage for the devices. The graph shows the transition from direct tunneling to Fowled-Nordheim tunneling confirming electron transport by tunneling. The figures show that the fabricated vertical tunneling junctions can be described by quantum tunneling and not by trap-assisted tunneling, which would show evidence of RTN.

C. Fabricating Lateral Electrical Tunneling Junctions

Lateral electrical tunneling junctions were fabricated to test tunneling current with different thicknesses of the insulating layers, different insulating materials, and different applied voltages.

Figure 14A:
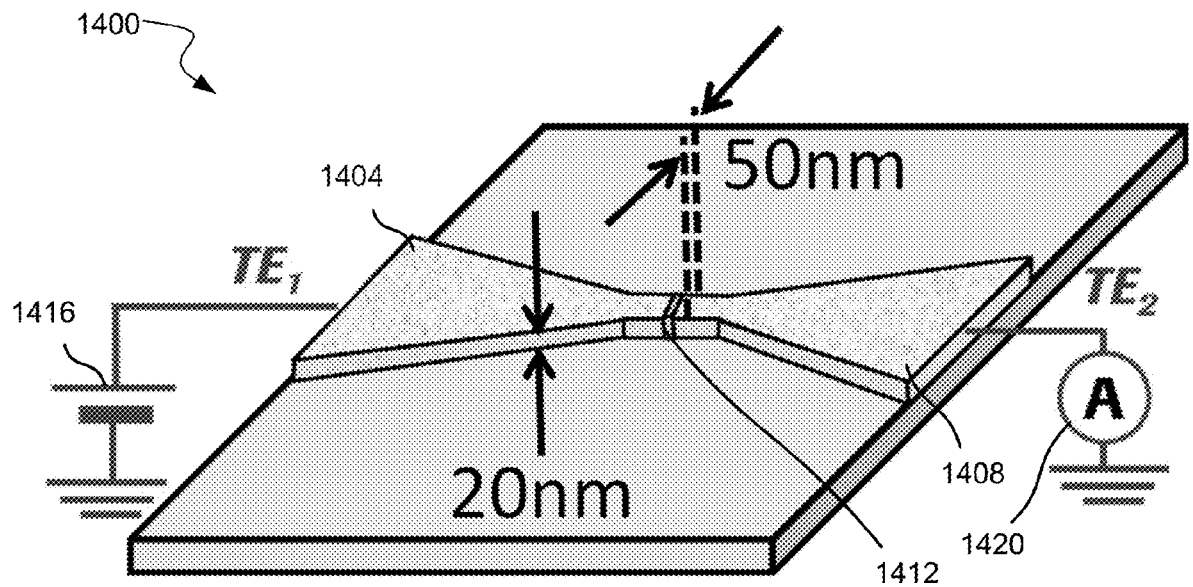
FIGS. 14A and 14B show depictions of a lateral electrical tunneling junction according to embodiments of the present invention.

FIG. 14A shows the configuration of a fabricated lateral tunneling junction device 1400. A first electrode 1404 and a second electrode 1408 are separated by an insulating layer 1412. First electrode 1404 and second electrode 1408 are both platinum. The material for insulating layer 1412 is alumina ($Al_2O_3$), hafnia ($HfO_2$), or magnesium oxide (MgO). First electrode 1404 and second electrode 1408 may be in electrical communication with a power supply 1416 and a current meter 1420. The thickness of each of first electrode 1404, second electrode 1408, and insulating layer 1412 is 20 nm. The width of first electrode 1404, second electrode 1408, and insulating layer 1412 adjacent to where the electrodes contact insulating layer 1412 is 50 nm. The junction area is 1,000 $nm^2$. The sensing area is 20 $nm^2$.

Figure 14B:
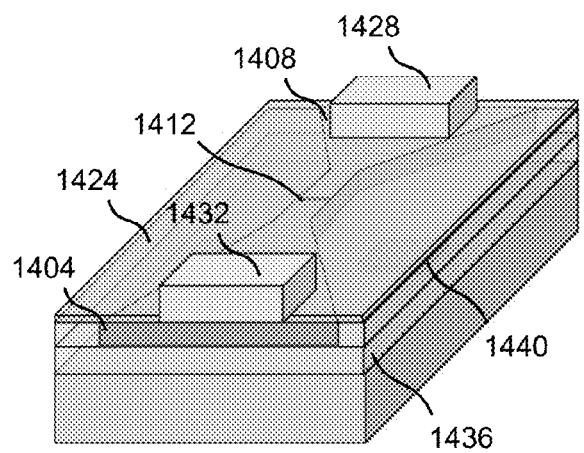

FIG. 14B is an illustration of a fabricated lateral tunneling junction. An insulating plane 1424 is disposed on top of first electrode 1404, second electrode 1408, and insulating layer 1412. Insulating plane 1424 may be silicon dioxide and may be deposited after the junction region is defined by CMP. Contacts 1428 and 1432 allow for electrical communication with the tunneling junction. The lateral tunneling junction is on top of substrate 1436. Mark 1440 is a metrology mark used to determine the height of the electrodes and is not needed for device functionality.

D. Electrical Results From Lateral Tunneling Junctions

FIGS. 15A, 15B, 15C, and 15D show electrical results from testing lateral electrical tunneling junctions with the configuration illustrated in FIG. 14B.

Figure 15A:
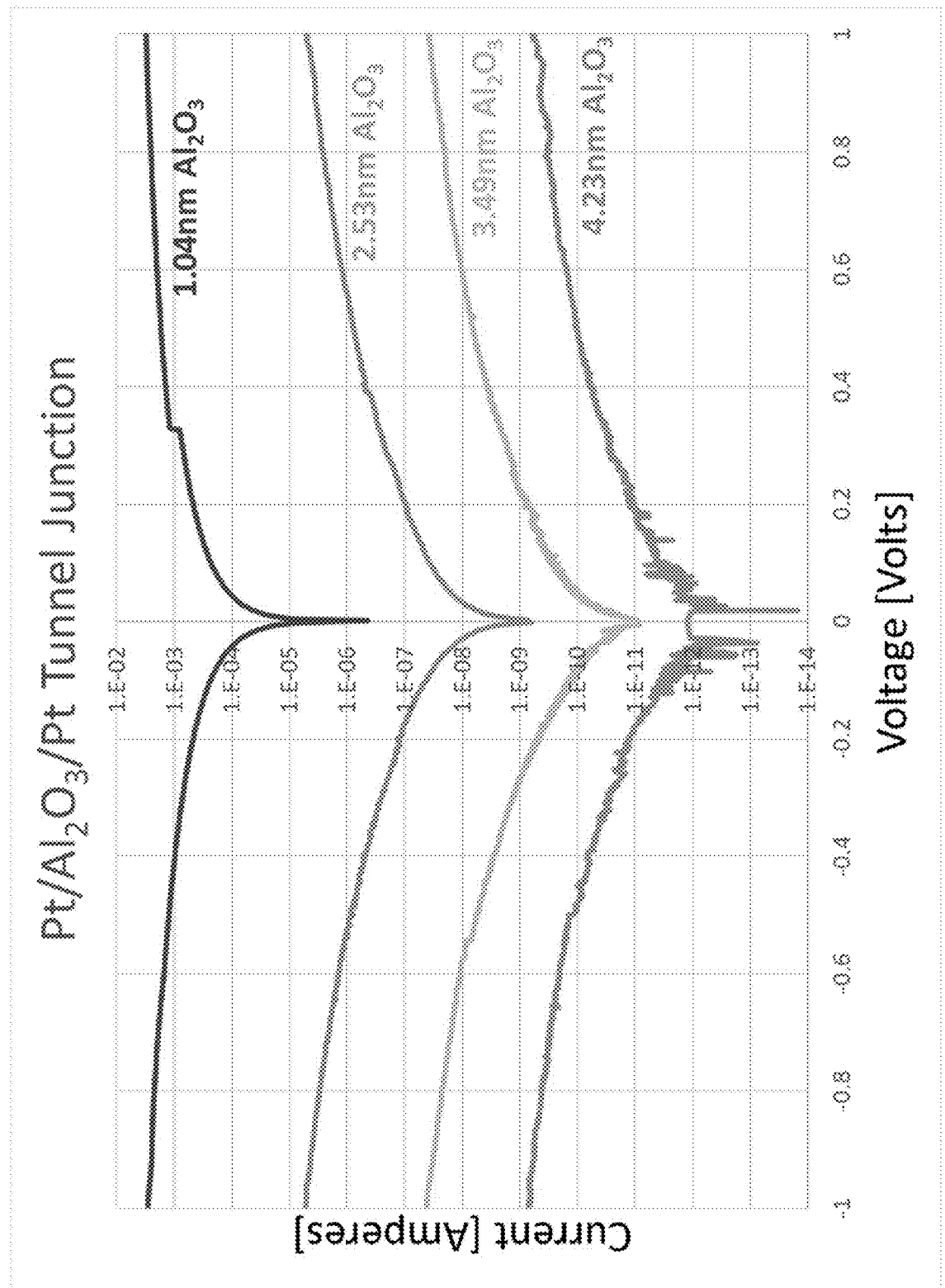
FIGS. 15A, 15B, 15C, and 15D show electrical results from testing lateral electrical tunneling junctions according to embodiments of the present invention.

FIG. 15A shows current versus voltage for different thicknesses of the $Al_2O_3$ insulating layer. The thicknesses tested were 1.04 nm, 2.54 nm, 3.49 nm, and 4.23 nm. A thicker insulating layer resulted in less tunneling current at different voltages.

Figure 15B:
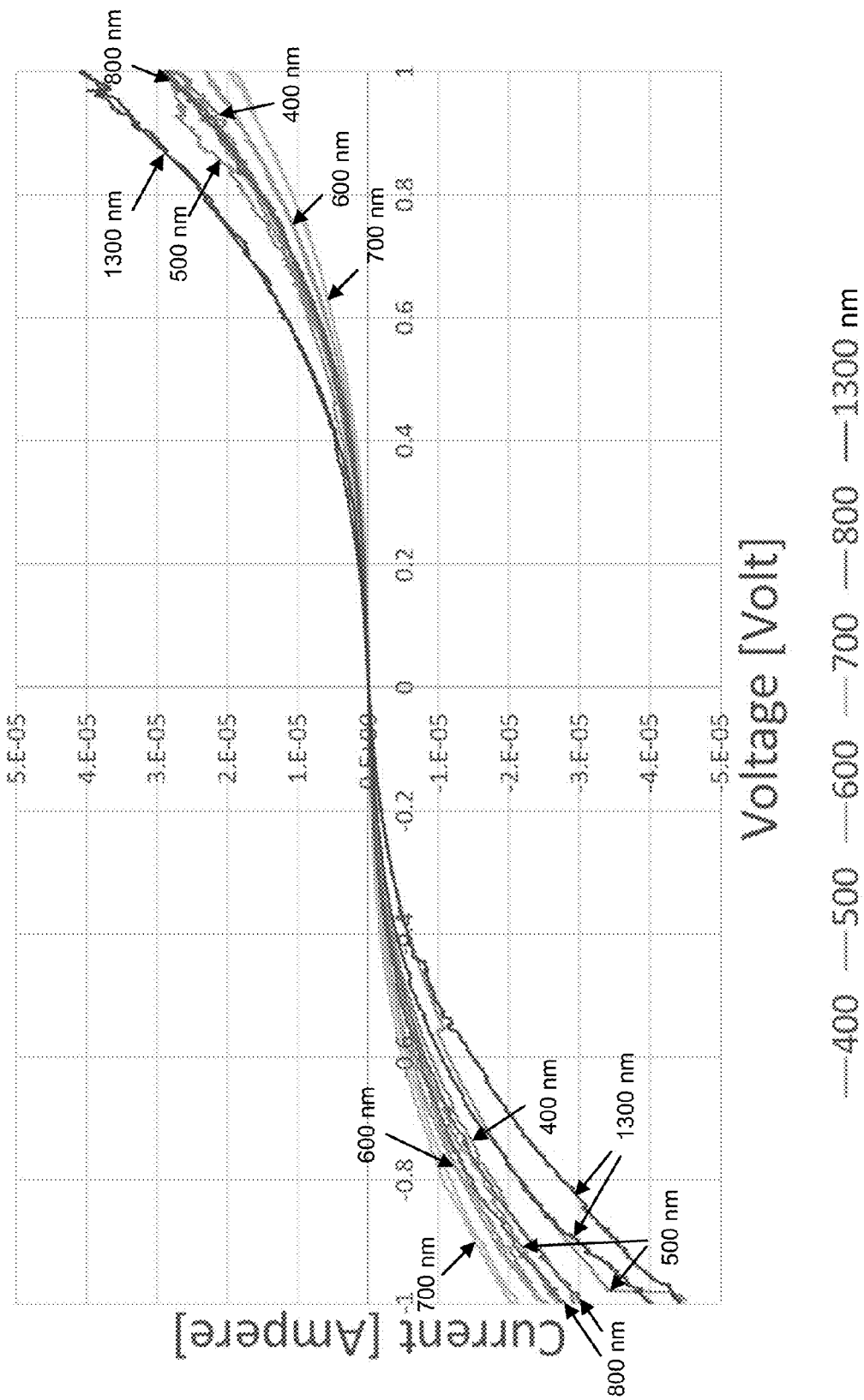

FIG. 15B shows the current versus voltage for a 2.53 nm thick insulating layer. The different lines are for junction widths of 400 nm, 500 nm, 600 nm, 700 nm, 800 nm, and 1,300 nm. The IV curves show rectifying behavior indicating electron transport by tunneling. Current fluctuations show evidence of RTN attributed to charge traps introduced during the fabrication process.

Figure 15C:
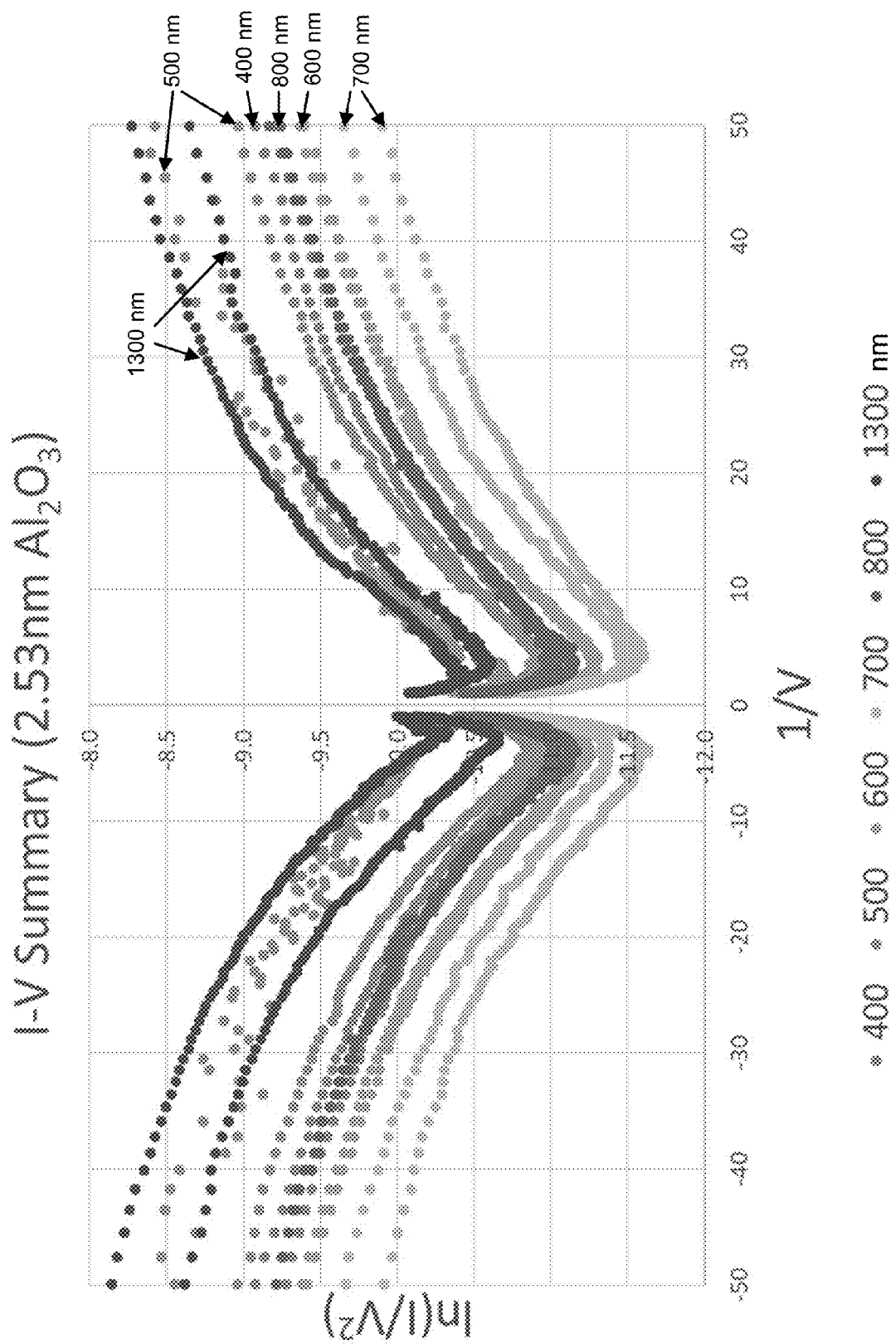

FIG. 15C shows the natural logarithm of the quantity of the current divided by the voltage squared versus the current divided by the voltage for devices with a 2.53 nm thick insulating layer.

Figure 15D:
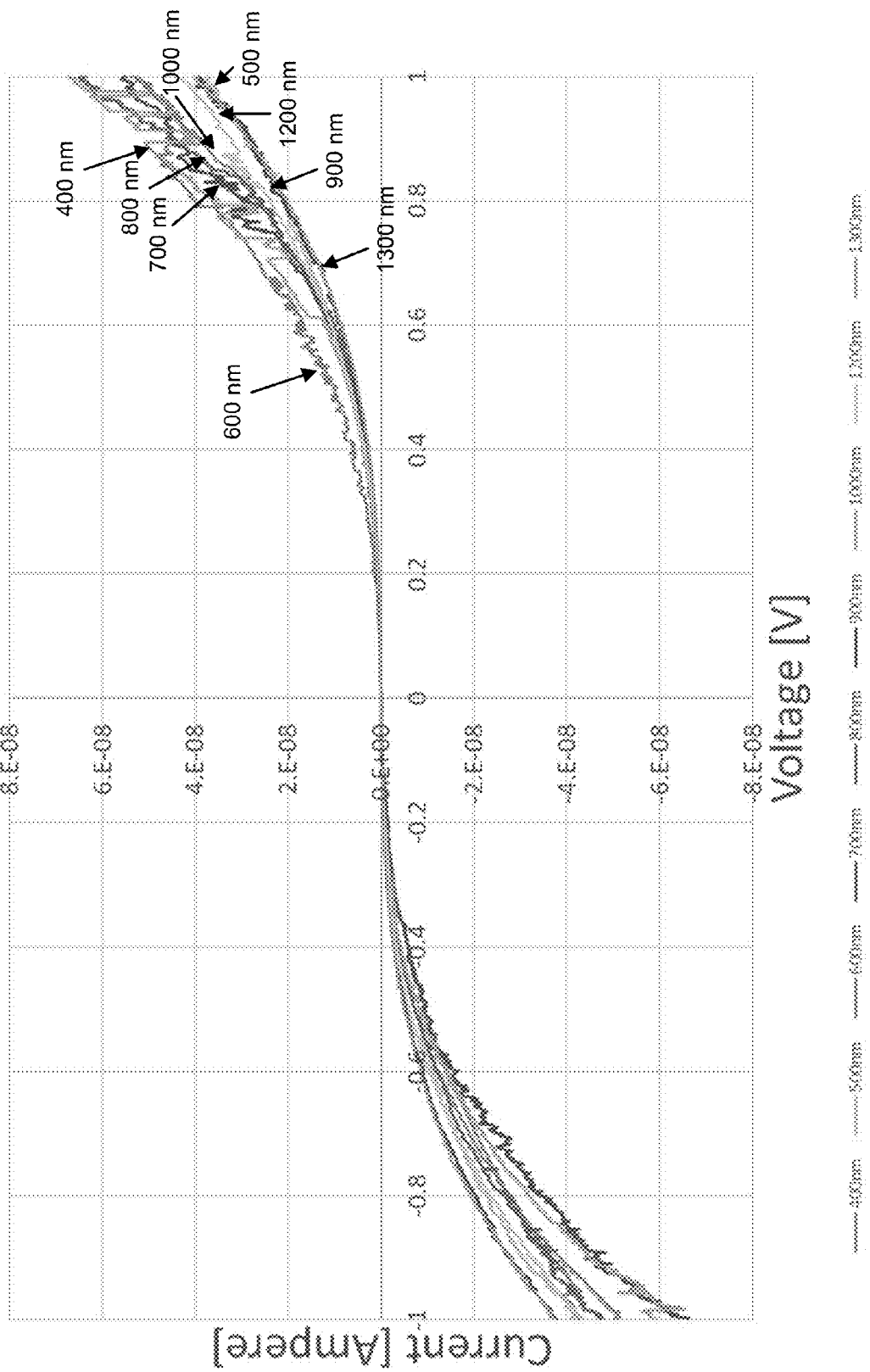

FIG. 15D shows the current versus voltage for a 3.49 nm thick insulating layer. The different lines are for junction widths of 400 nm, 500 nm, 600 nm, 700 nm, 800 nm, and 1,300 nm. The IV curves show rectifying behavior indicating electron transport by tunneling. Current fluctuations show evidence of RTN attributed to charge traps introduced during the fabrication process.

VI. EXAMPLE SYSTEMS

Figure 16:
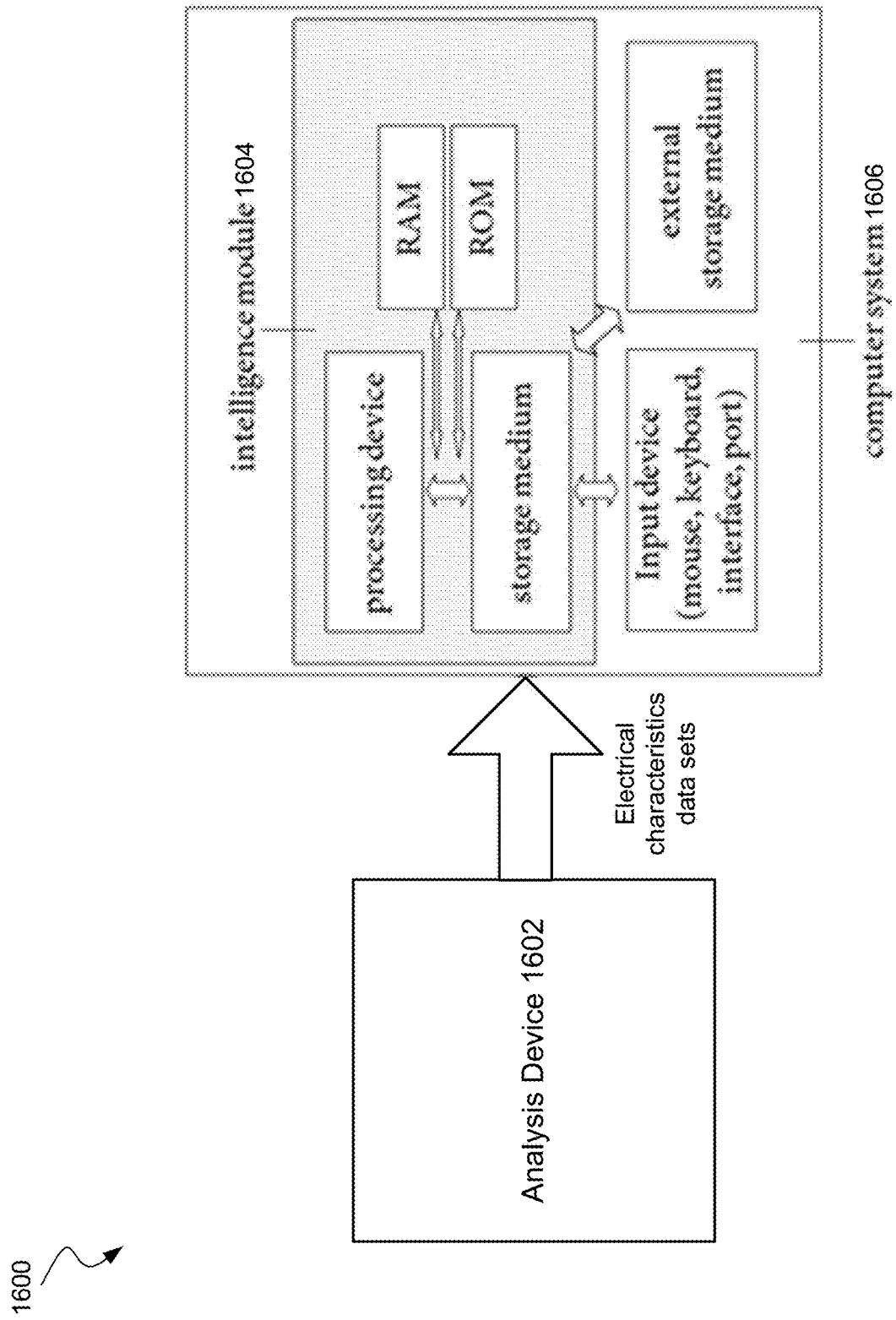
FIG. 16 shows an analysis system according to embodiments of the present invention.

FIG. 16 shows an exemplary analysis system. The system depicted in FIG. 16 comprises an analysis device 1602 and an intelligence module 1604 that is part of the computer system 1606. Analysis device 1602 may include system 900, system 1000, or any system described herein. Computer system 1606 may include parts or all of computer system 10. The data sets (electrical characteristics data sets) are transferred from the analysis device 1602 to the intelligence module 1604 or vice versa via a network connection or a direct connection. The data sets may for example be processed to identify nucleotides. The identification steps may be implemented by software stored on the hardware of computer system 1606. The data sets may be processed by computer code running on the processor and being stored on the storage device of the intelligence module and after processing transferred back to the storage device of the analysis module, where the modified data may be displayed on a displaying device. In some embodiments, the intelligence module may also be implemented in the analysis device.

Figure 17:
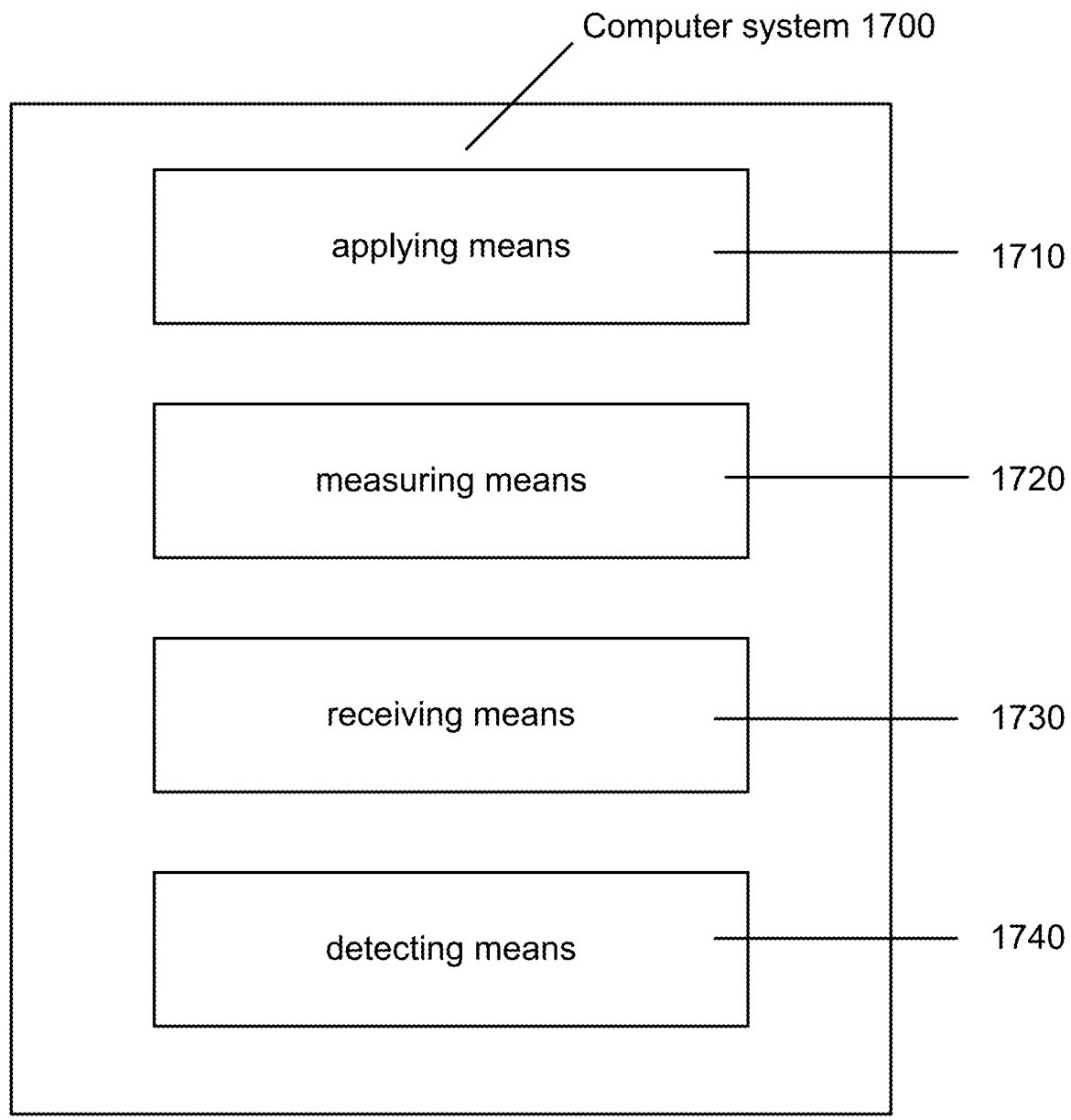
FIG. 17 shows a computer system according to embodiments of the present invention.

FIG. 17 shows that computer system 1700 may comprise applying means 1710, which may include, for example, applying a voltage across a first electrode and a second electrode separated by an insulating layer. Computer system 1700 may be a field-programmable gate array (FPGA) or application-specific integrated circuit (ASIC) computer. Computer system 1700 may also include measuring means 1720, which may include measuring a value of an electrical characteristic through the first electrode and the second electrode. Computer system 1700 may further include receiving means, which may include receiving the value of an electrical characteristic from an analysis system. Computer system 1700 may also include detecting means, which may include, for example, detecting a nucleotide as being hybridized to the template parent strand using the value of the electrical characteristic.

Figure 18:
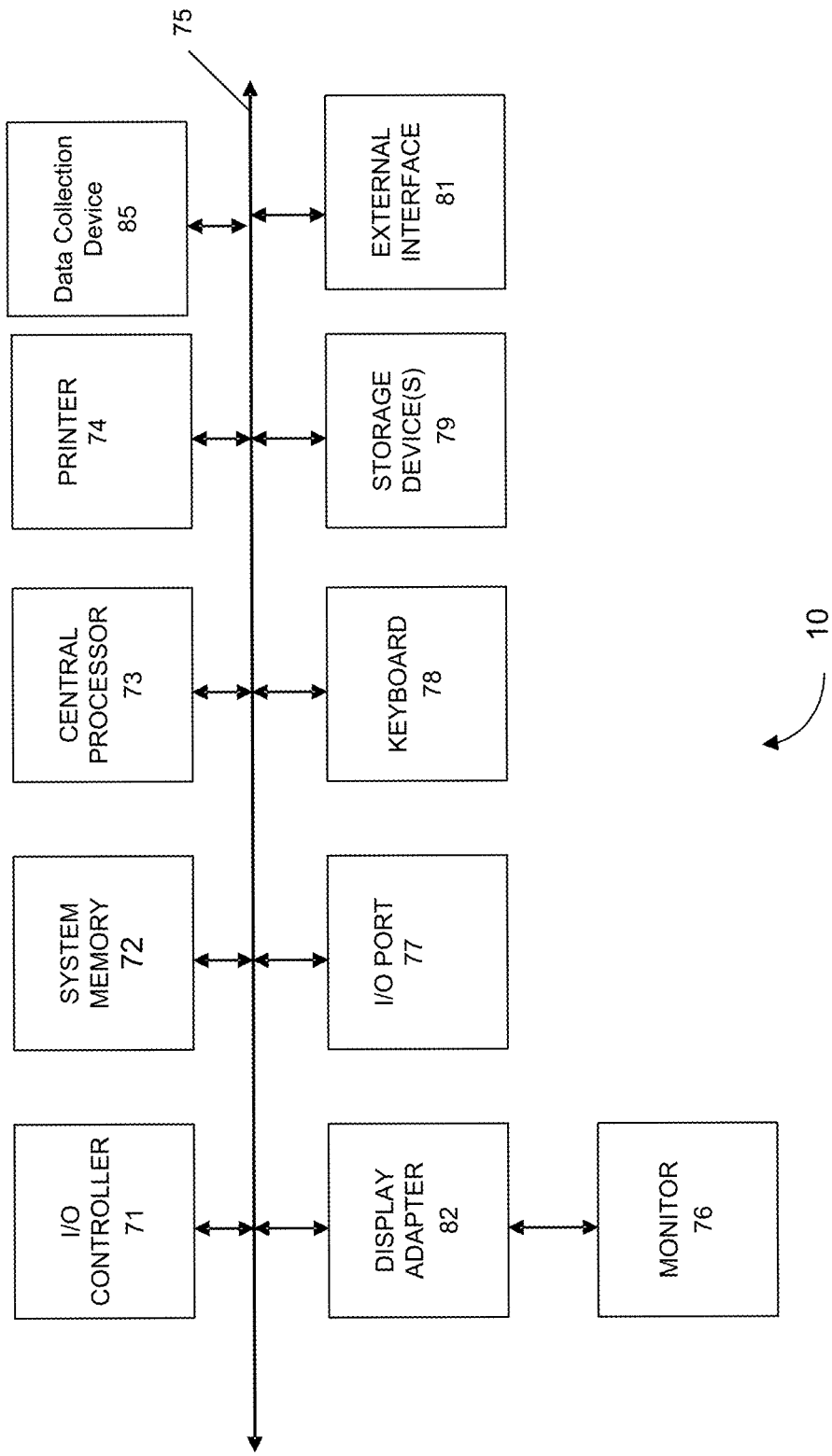
FIG. 18 shows a computer system according to embodiments of the present invention.

Any of the computer systems mentioned herein may utilize any suitable number of subsystems. Examples of such subsystems are shown in FIG. 18 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices. Computer system 10 may be a field-programmable gate array (FPGA) or application-specific integrated circuit (ASIC) computer.

The subsystems shown in FIG. 18 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire®, Thunderbolt). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, units, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

In the preceding description, for the purposes of explanation, numerous details have been set forth in order to provide an understanding of various embodiments of the present technology. It will be apparent to one skilled in the art, however, that certain embodiments may be practiced without some of these details, or with additional details.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Additionally, details of any specific embodiment may not always be present in variations of that embodiment or may be added to other embodiments.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a method" includes a plurality of such methods and reference to "the moiety" includes reference to one or more moieties and equivalents thereof known to those skilled in the art, and so forth. The invention has now been described in detail for the purposes of clarity and understanding. However, it will be appreciated that certain changes and modifications may be practice within the scope of the appended claims.

All publications, patents, and patent applications cited herein are hereby incorporated by reference in their entirety for all purposes. None is admitted to be prior art.

What is claimed is:

1. A method of determining a sequence of a nucleic acid using a sequencing device, the method comprising:
   adding a set of nucleotides to the sequencing device, wherein:
      each nucleotide of the set of nucleotides is attached to a label compound comprising a moiety,
      the sequencing device comprises a tunneling junction, and
      the tunneling junction comprises a first conductor and a second conductor separated by an insulating layer, wherein:
         the thickness of the insulating layer separating the first conductor and the second conductor is greater than the size of each moiety of each nucleotide of the set of nucleotides,
         the first conductor comprises a first ferromagnetic material, and
         the second conductor comprises a second ferromagnetic material;
   elongating a nascent strand using a polymerase attached to the tunneling junction and connected to a template parent strand to be sequenced, wherein the elongating includes the polymerase incorporating a first nucleotide of the set of nucleotides into the nascent strand via hybridization to the template parent strand;
   measuring a value of an electrical characteristic or a magnetic characteristic through the first conductor, a first moiety of a first label compound attached to the first nucleotide, and the second conductor; and
   detecting the first nucleotide as being hybridized to the template parent strand using the value of the electrical characteristic or the magnetic characteristic.

2. The method of claim 1, wherein:
   the first conductor is a first electrode, the second conductor is a second electrode,
measuring the value of the electrical characteristic or the magnetic characteristic comprises measuring the value of the electrical characteristic, and
detecting the first nucleotide as being hybridized to the template parent strand comprises using the value of the electrical characteristic, and
the method further comprising:
applying a voltage across the first conductor and the second conductor.

3. The method of claim 2, wherein detecting the first nucleotide as being hybridized to the template parent strand based on the value of the electrical characteristic comprises:
comparing the value of the electrical characteristic to a reference value of the electrical characteristic, and
determining the value exceeds the reference value.

4. The method of claim 3, wherein the reference value is of a background tunneling current that is through the first electrode and the second electrode and that does not pass through the moiety.

5. The method of claim 2, wherein the electrical characteristic is current, and the value is greater than 10 nA.

6. The method of claim 2, wherein the moiety is selected from the group consisting of an organometallic compound, a nanoparticle, a conjugated aromatic, and a conductive organic molecule.

7. The method of claim 2, wherein the label compound comprises a terminator configured to prevent further elongation of the nascent strand.

8. The method of claim 2, wherein:
each nucleotide of the set of nucleotides is a same type of nucleotide, and
each moiety of each label compound attached to each nucleotide of the set of nucleotides is a same type of moiety.

9. The method of claim 2, wherein:
the set of nucleotides comprises a second nucleotide attached to a second label compound comprising a second moiety,
detecting the first nucleotide as being hybridized to the template parent strand based on the value of the electrical characteristic comprises:
comparing the value of the electrical characteristic to a first reference value of the electrical characteristic,
the method further comprising:
determining the second nucleotide is not being hybridized to the template parent strand based on the value of the electrical characteristic by comparing the value of the electrical characteristic to a second reference value of the electrical characteristic.

10. The method of claim 2, wherein:
the sequencing device comprises a plurality of tunneling junctions,
each tunneling junction comprises a respective first electrode, a respective second electrode, and a respective insulating layer, and
each respective tunneling junction is attached to a respective polymerase,
the method further comprising:
for each tunneling junction of the plurality of tunneling junctions:
elongating a respective nascent strand using the respective polymerase attached to the respective tunneling junction and connected to a respective template parent strand to be sequenced, wherein the elongating includes the respective polymerase incorporating a respective nucleotide of the set of nucleotides into the respective nascent strand via hybridization to the respective template parent strand,
applying a respective voltage across the respective first electrode and the respective second electrode of the respective tunneling junction,
measuring a respective value of the electrical characteristic through the respective first electrode, the respective moiety of a respective label compound attached to the respective nucleotide, and the respective second electrode, and
detecting the respective nucleotide as being hybridized to the respective template parent strand using the respective value of the electrical characteristic.

11. The method of claim 10, further comprising:
removing remaining nucleotides of the set of nucleotides that have not been incorporated into a nascent strand, wherein removing the set of nucleotides occurs before measuring the value of the electrical characteristic.

12. The method of claim 11, wherein removing the set of nucleotides except the first nucleotide from contacting the tunneling junction comprises rinsing the tunneling junction with water.

13. The method of claim 11, wherein:
the set of nucleotides is a first set of nucleotides, and
the value of the electrical characteristic is a first value of the electrical characteristic,
the method further comprising:
cleaving the first label compound from the first nucleotide,
adding a second set of nucleotides to the sequencing device, each nucleotide of the second set of nucleotides attached to a second label compound comprising a second moiety, each nucleotide of the set of nucleotides being a different type of nucleotide than the first nucleotide, each second moiety the same as the first moiety,
elongating the nascent strand by the polymerase, wherein the elongating includes the polymerase incorporating a second nucleotide of the second set of nucleotides into the nascent strand via hybridization to the template parent strand,
measuring a second value of the electrical characteristic through the first electrode, the second moiety of the second label compound attached to the second nucleotide, and the second electrode, and
detecting the second nucleotide as being hybridized to the template parent strand based on the second value of the electrical characteristic.

14. The method of claim 1, wherein the first ferromagnetic material is a permanent magnet with a first polarity, the method further comprising:
applying a magnetic field to set a second polarity of the second ferromagnetic material to be anti-parallel to the first polarity.

15. The method of claim 1, wherein:
measuring the value of the electrical characteristic or the magnetic characteristic comprises measuring the value of the electrical characteristic,
detecting the first nucleotide as being hybridized to the template parent strand comprises using the value of the electrical characteristic, and
the electrical characteristic is a current.

16. The method of claim 15, wherein detecting the first nucleotide as being hybridized to the template parent strand using the value of the electrical characteristic comprises:

comparing the value of the electrical characteristic to a reference value of the electrical characteristic, and determining the value exceeds the reference value.

17. The method of claim 16, wherein the reference value is of a background current through the first conductor, the insulating layer, and the second conductor.

18. The method of claim 1, wherein the first moiety is an organometallic group.

19. The method of claim 18, wherein the organometallic group comprises ferrocene, metal phthalocyanines, ruthenium, osmium, or transition metal organometallic compounds.

20. The method of claim 1, wherein the first moiety is a nanoparticle.

21. The method of claim 20, wherein the nanoparticle comprises gold, silver, platinum, magnesium, or titanium nitride.

22. The method of claim 20, wherein the nanoparticle has a characteristic size from 1 to 10 nm.

23. The method of claim 1, wherein the first moiety is a conjugated aromatic group.

24. The method of claim 23, wherein the conjugated aromatic group comprises anthracene, phenanthrene, tetracene, chrysene, triphenylene, pyrene, pentacene, benzopyrene, corannulene, benzoperylene, coronene, ovalene, or benzofluorene.

25. The method of claim 1, wherein the first moiety is a conductive organic molecule.

26. The method of claim 25, wherein the conductive organic molecule is poly-pyrrole or poly-aniline.

27. The method of claim 1, wherein the first label compound comprises a cleavable linker and a spacer.

28. The method of claim 27, wherein the spacer comprises a polyethylene glycol (PEG), an alkyl or aryl spacer, a peptide, a cationic spacer, a nucleic acid, or a carbohydrate.

29. The method of claim 1, wherein the tunneling junction is circular.

30. The method of claim 1, wherein the first conductor has a width adjacent to the insulating layer from 35 nm to 65 nm.

31. The method of claim 1, wherein the first conductor has a height from 10 nm to 30 nm.

32. The method of claim 1, wherein the thickness of the insulating layer is greater than 2 nm.

33. A method of determining a sequence of a nucleic acid using a sequencing device, the method comprising:

adding a set of nucleotides to the sequencing device, wherein:

each nucleotide of the set of nucleotides is attached to a label compound comprising a moiety, the sequencing device comprises a tunneling junction, and the tunneling junction comprises a first conductor and a second conductor separated by an insulating layer, wherein the first conductor comprises a first ferromagnetic material, and the second conductor comprises a second ferromagnetic material;

elongating a nascent strand using a polymerase attached to the tunneling junction and connected to a template parent strand to be sequenced, wherein the elongating includes the polymerase incorporating a first nucleotide of the set of nucleotides into the nascent strand via hybridization to the template parent strand;

measuring a value of an electrical characteristic or a magnetic characteristic through the first conductor, a first moiety of a first label compound attached to the first nucleotide, and the second conductor; and detecting the first nucleotide as being hybridized to the template parent strand using the value of the electrical characteristic or the magnetic characteristic.

34. The method of claim 33, wherein the first ferromagnetic material is a permanent magnet with a first polarity, the method further comprising:

applying a magnetic field to set a second polarity of the second ferromagnetic material to be anti-parallel to the first polarity.

35. The method of claim 33, wherein:

measuring the value of the electrical characteristic or the magnetic characteristic comprises measuring the value of the electrical characteristic, detecting the first nucleotide as being hybridized to the template parent strand comprises using the value of the electrical characteristic, and the electrical characteristic is a current.

36. The method of claim 35, wherein detecting the first nucleotide as being hybridized to the template parent strand using the value of the electrical characteristic comprises:

comparing the value of the electrical characteristic to a reference value of the electrical characteristic, and determining the value exceeds the reference value.

37. The method of claim 36, wherein the reference value is of a background current through the first conductor, the insulating layer, and the second conductor.

38. The method of claim 33, wherein the first moiety is a ferromagnetic or superparamagnetic material.

39. The method of claim 38, wherein the first moiety is a magnetic nanoparticle.

40. The method of claim 39, wherein the magnetic nanoparticle is FePt, FeCuPt, or $Fe_2O_3$.

41. The method of claim 39, wherein the magnetic nanoparticle has a diameter less than 1 µm.

42. The method of claim 39, wherein the magnetic nanoparticle has a diameter less than 10 nm.

43. The method of claim 33, wherein the tunneling junction is circular.

* * * * *